US009000151B2

(12) United States Patent
Adamski-Werner et al.

(10) Patent No.: US 9,000,151 B2
(45) Date of Patent: Apr. 7, 2015

(54) SWEET FLAVOR MODIFIER

(71) Applicant: Senomyx, Inc., San Diego, CA (US)

(72) Inventors: Sara L. Adamski-Werner, San Diego, CA (US); Vincent Darmohusodo, Encinitas, CA (US); Catherine Tachdjian, San Diego, CA (US); Donald S. Karanewsky, Escondido, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 14/184,245

(22) Filed: Feb. 19, 2014

(65) Prior Publication Data

US 2014/0235624 A1 Aug. 21, 2014

Related U.S. Application Data

(60) Provisional application No. 61/766,652, filed on Feb. 19, 2013.

(51) Int. Cl.
 *C07D 417/14* (2006.01)
 *C07D 417/12* (2006.01)

(52) U.S. Cl.
 CPC ............ *C07D 417/14* (2013.01); *C07D 417/12* (2013.01)

(58) Field of Classification Search
 USPC .......................................................... 544/11
 See application file for complete search history.

(56) References Cited

U.S. PATENT DOCUMENTS

| 3,278,532 | A  | 10/1966 | Houlihan |
| 3,843,804 | A  | 10/1974 | Evers et al. |
| 3,845,770 | A  | 11/1974 | Theeuwes et al. |
| 3,857,972 | A  | 12/1974 | Evers et al. |
| 3,916,899 | A  | 11/1975 | Theeuwes et al. |
| 3,957,783 | A  | 5/1976 | Hirohashi et al. |
| 3,960,860 | A  | 6/1976 | Katz et al. |
| 4,146,716 | A  | 3/1979 | Cox et al. |
| 4,196,207 | A  | 4/1980 | Webber et al. |
| 4,377,580 | A  | 3/1983 | Ueda et al. |
| 4,765,539 | A  | 8/1988 | Noakes et al. |
| 5,112,598 | A  | 5/1992 | Biesalski |
| 5,380,541 | A  | 1/1995 | Beyts et al. |
| 5,504,095 | A  | 4/1996 | Nakane et al. |
| 5,556,611 | A  | 9/1996 | Biesalski |
| 5,698,155 | A  | 12/1997 | Grosswald et al. |
| 5,801,180 | A  | 9/1998 | Takase et al. |
| 5,950,619 | A  | 9/1999 | van der Linden et al. |
| 5,954,047 | A  | 9/1999 | Armer et al. |
| 5,970,974 | A  | 10/1999 | van der Linden et al. |
| 5,990,117 | A  | 11/1999 | Pamukcu et al. |
| 6,046,206 | A  | 4/2000 | Pamukcu et al. |
| 6,316,454 | B1 | 11/2001 | Uckun et al. |
| 7,105,650 | B2 | 9/2006 | Adler |
| 7,915,410 | B2 | 3/2011 | Johnson et al. |
| 7,928,111 | B2 | 4/2011 | Tachdjian et al. |
| 8,541,421 | B2 | 9/2013 | Tachdjian et al. |
| 8,633,186 | B2 | 1/2014 | Tachdjian et al. |
| 2003/0008344 | A1 | 1/2003 | Adler et al. |
| 2003/0054448 | A1 | 3/2003 | Adler et al. |
| 2003/0232407 | A1 | 12/2003 | Zoller et al. |
| 2004/0127435 | A1 | 7/2004 | Carson et al. |
| 2005/0032158 | A1 | 2/2005 | Adler et al. |
| 2006/0045953 | A1 | 3/2006 | Tachdjian et al. |
| 2006/0134693 | A1 | 6/2006 | Servant et al. |
| 2006/0135552 | A1 | 6/2006 | Malherbe et al. |
| 2007/0104709 | A1 | 5/2007 | Li et al. |
| 2008/0306053 | A1 | 12/2008 | Tachdjian et al. |
| 2008/0306093 | A1 | 12/2008 | Servant et al. |
| 2011/0224155 | A1 | 9/2011 | Tachdjian et al. |
| 2011/0230502 | A1 | 9/2011 | Tachdjian et al. |
| 2014/0094453 | A1 | 4/2014 | Tachdjian et al. |

FOREIGN PATENT DOCUMENTS

| DE | 22 58 403 A1 | 6/1973 |
| EP | 0530994 A1 | 3/1993 |
| RU | 2241436 C2 | 12/2004 |
| WO | WO 03/001876 A2 | 1/2003 |
| WO | WO 03/004992 A2 | 1/2003 |

(Continued)

OTHER PUBLICATIONS

Albrecht et al., "Synthesis of 1,2,6-Thiadiazine 1,1-Dioxides via Isoxazolylsulfamides," J. Org. Chem. 44:4191-4194 (1979).

Alderman, "A Review of Cellulose Ethers in Hydrophilic Matrices for Oral Controlled-Release Dosage Forms," Int. J. Pharm. Tech. & Prod. Mfr. 5(3):1-9 (1984).

Bamba et al., "Release mechanisms in Gelforming Sustained Release Preparations," Int. J. Pharm. 2:307-315 (1979).

Bandurco et al., "Synthesis and Cardiotonic Activity of a Series of Substituted 4-Alkyl-2(1H)-quinazolinones," J. Med. Chem. 30:1421-1426 (1987).

Belikov V.G., Farmatsevticheskaya khimiya, M., Visshaya shkola, 1993, pp. 43-47.

(Continued)

*Primary Examiner* — Kahsay Habte
(74) *Attorney, Agent, or Firm* — Knobbe Martens Olson & Bear LLP

(57) ABSTRACT

The present invention includes compounds having structural formula (I):

or salts or solvates thereof. These compounds are useful as sweet flavor modifiers. The present invention also includes compositions comprising the present compounds and methods of enhancing the sweet taste of compositions.

13 Claims, No Drawings

(56) References Cited

FOREIGN PATENT DOCUMENTS

| WO | WO 03/022214 A2 | 3/2003 |
|---|---|---|
| WO | WO 03/051878 A1 | 6/2003 |
| WO | WO 03/055866 A1 | 7/2003 |
| WO | WO 2005/015158 A2 | 2/2005 |
| WO | WO 2005/116069 A2 | 12/2005 |
| WO | WO 2006/076102 A2 | 7/2006 |
| WO | WO 2006/084184 A2 | 8/2006 |
| WO | WO 2006/113422 A2 | 10/2006 |
| WO | WO 2006/113432 A2 | 10/2006 |
| WO | WO 2007/004709 A1 | 1/2007 |
| WO | WO 2007/047988 A2 | 4/2007 |
| WO | WO 2007/071963 A2 | 6/2007 |
| WO | WO 2008/003378 A1 | 1/2008 |
| WO | WO 2008/154221 A2 | 12/2008 |
| WO | WO 2012/054526 A2 | 12/2008 |
| WO | WO 2012/021837 A2 | 2/2012 |

OTHER PUBLICATIONS

Bellur et al., "Synthesis of 4-(3-hydroxyalkyl)pyrimidines by ring transformation reactions of 2-alkylidenetetrahydrofurans with amidines," Tetrahedron 62:5426-5434 (2006).

Berge et al., "Pharmaceutical Salts," J. Pharm. Sci. 66(1):1-19 (1977).

Bhattacharya et al., "Thieno[3',2' :4,5][1]benzothieno[2,3-d] pyrimidine derivatives: synthesis and conformation," J. Chem. Soc. Perkin Trans. 1, 1994, 6: 689-693.

Blackburn et al., "Identification and characterization of aminopiperidinequinolones and quinazolinones as MCHr1 antagonists," Bioorg. & Med. Chem. Lett. 16:2621-2627 (2006).

Boarland et al., "Monosubstituted Pyrimidines, and the Action of Thiourea on Chloropyrimidines," J. Chem. Soc. 1218-1221 (1951).

Brown, et al., "Evolution of a Series of Peptidoleukotriene Antagonists: Synthesis and Structure-Activity Relationships of 1,6-Disubstituted Indoles and Indazoles," J. Med. Chem. 33:1771-1781 (1990).

Buck et al., "A Novel Multigene Family May Encode Odorant Receptors: A Molecular Basis for Odor Recognition," Cell 65(1):175-187 (1991).

Campillo et al., "A study of peculiar tautomerism of pyrido[2,3-c][1,2,6]thiadiazine 2,2-dioxide system," J. Mol. Struct. 678:83-89 (2004).

Campillo et al., " A Novel Tetracyclic System Containing the 1,2,6-Thiadiazine Ring: Synthesis, Structural Assignment and Tautomeric Studies," Heterocycles, 1998, 48(3): 1833-1840.

Chandrashekar et al., "T2Rs Function as Bitter Taste Receptors," Cell 100:703-711 (2000).

Cheng et al., "Potential Purine Antagonists. XII. Synthesis of 1-Alkyl(aryl)-4,6-disubstituted Pyrazolo[3,4-d]pyrimidines" Journal of Organic Chemistry, Jun. 1, 1958 23(1):852-861.

Chien et al., "Nucleosides XI. Synthesis and Antiviral Evaluation of 5'-Alkylthio-5'-deoxy Quinazolinone Nucleoside Derivatives as S-Adenosyl-L-homocysteine Analogs," Chem. Pharm. Bull. 52(12):1422-1426 (2004).

Clauß et al., "Cycloadditionen von Halogensulfonylisocyanaten an Acetylene," Tetrahedron Lett. 2:119-122 (1970).

Corbett et al., "Novel 2,2-Dioxide-4,4-disubstituted-1,3-H-2,1,3-benzothiadiazines as Non-Nucleside Reverse Transcriptase Inhibitors," Bioorg. Med. Chem. Lett. 10:193-195 (2000).

Da Settimo et al.,"Naphtho[1,2-d]isothiazole Acetic Acid Derivatives as a Novel Class of Selective Aldose Reductase Inhibitors," J. Med. Chem. 48:6897-6907 (2005).

Dominguez et al., "Efficient synthesis of 4,4-disubstituted-3,4-dihydro-1H-2,1,3-benzothiadiazine 2,2-dioxides," Tetrahedron Lett. 41:9825-9828 (2000).

Dorwald, "Side Reactions in Organic Synthesis: A Guide to Successful Synthesis Design," Weinheim: WILEY-VCH Verlag Gmbh & o. KGaA, 2005, ISBN: 3-527-31021-5.

During et al., "Controlled Release of Dopamine from a Polymeric Brain Implant: In Vivo Characterization," Ann. Neurol. 25:351-356 (1989).

Elmegeed et al., "Novel synthesizes aminosteroidal heterocycles intervention for inhibiting iron-induced oxidative stress," Eur. J. Med. Chem. 40:1283-1294 (2005).

El-Sherbeny et al., "Novel Pyridothienopyrimidine and Pyridothienothiazine Derivatives as Potential Antiviral and Antitumor Agents," Med. Chem. Res. 10:122-135 (2000).

Etter et al., "An Enolized Sulfonamide Formed by Strong Hydrogen Bonding to Triphenylphosphine Oxide," J. Org. Chem. 51:5405-5408 (1986).

European Search Opinion based on EP Application No. 08770047.2, mailed on Sep. 14, 2009.

European Search Report, EP Appl. No. 12175764.5, 16 pages (Feb. 22, 2013).

Francis et al., "Anxiolytic Properties of Certain Annelated [1,2,4]Triazolo[1,5-c]pyrimidin-5(6H)-ones," J. Med. Chem. 34:2899-2906 (1991).

Frauli et al., "Amino-Pyrrolidine Tricarboxylic Acids Give New Insight into Group III Metabotropic Glutamate Receptor Activation Mechanism," Mol. Pharmacol. 71:704-712 (2007).

Garcia-Munoz et al., "Synthesis of Purine-Like Ring Systems Derived From 1,2,6-Thiadiazine 1,1-Dioxide," J. Heterocyclic Chem. 13:793-796 (1976).

Goya and Martinez, "Synthesis and Cytostatic Screening of an SO2 Analogue of Doridosine," Arch. Pharm. (Weinheim) 321:99-101 (1988).

Goya and Paez, "Pteridine Analogues; Synthesis and Physico-Chemical Properties of 7-Oxopyrazino [2,3-c][1,2,6] thiadiazine 2,2-Dioxides," Liebigs Ann. Chem., 121-124 (1988).

Goya et al., "Aminopyrido [2,3-c] [1,2,6] Thiadiazine 2,2-Dioxides: Synthesis and Physico-chemical Properties," Chemica Scripta, 26:607-611 (1986).

Goya et al., "Fused 1,2,6-Thiadiazines: Tetrahydrobenzo[b]thieno[2,3-c] [1,2,6]thiadiazine 2,2-Dioxides," Arch. Pharm. (Weinheim) 317:777-781 (1984).

Goya et al., "N-Glucosyl-5-Amino-4-Carbamoyl- and 4-Ethoxycarbonylimidazoles as Potential Precursors of 4-0xoimidazo[4,5-c]-1,2,6-thiadiazine 2,2-Dioxides," Heterocycles 24:3451-3458 (1986).

Goya et al., "Synthesis of 2S-Dioxo Isosteres of Purine and Pyrimidine Nucleosides IV. Selective Glycosylation of 4-Amino-5H-Imidazo [4,5-c] -1,2,6-Thiadiazine 2,2-Dioxide," Nucleosides & Nucleotides, 6(3), 631-642 (1987).

Goya et al., CAPLUS Accession No. 1987:18628, 2 pages, abstract of ES 531159 A1 (1985).

Hauser et al., "Synthesis of 5-Phenyl-4,6-Dimethyl-2-Pyrimidol and Derivatives from the Cyclization of Urea with 3-Phenyl-2,4-Pentanedione," J. Org. Chem. 18:588-593 (1953).

Hirayama et al., "The Discovery of YM-60828: A Potent, Selective and Orally-Bioavailable Factor Xa Inhibito," Bioorg. & Med. Chem. 10:1509-1523 (2002).

Hirohashi et al. "Nuclear magnetic resonance studies of bicyclic thiophene derivatives. I ring current effects of the benzene ring on the H.alpha. and H.beta. signals of the thiophene ring in benzoylthiophene, thienopyrimidine, and thienodiazepine derivatives" Bulletin of The Chemical Society of Japan, 48(1), 147-156 (1975).

Hirota et al., "Synthesis and Biological Evaluation of 2,8-Disubstituted 9-Benzyladenines: Discovery of 8-Mercaptoadenines as Potent Interferon-Inducers," Bioorg. Med. Chem. 11:2715-2722 (2003).

Hoon et al., Putative Mammalian Taste Receptors: A Class of Taste-Specific GPCRs with Distinct Topographic Selectivity. Cell 96:541-551 (1991).

Howard et al., "Intracerebral drug delivery in rats with lesion-induced memory deficits," J. Neurosurg. 71:105-112 (1989).

Hu et al., "Organic Reactions in Ionic Liquids: Gewald Synthesis of 2-Aminothiophenes Catalyzed by Ethylenediammonium Diacetate," Synthetic Communication 34:3801-3806 (2004).

International Search Report, 5 pages, PCT Appl. No. PCT/US2008/065650 (mailed Nov. 20, 2008).

International Search Report, PCT appl. No. PCT/US2013/053666, 4 pages (Dec. 9, 2013).

(56) References Cited

OTHER PUBLICATIONS

Jordan, "Tamoxifen: A Most Unlikely Pioneering Medicine," Nature Reviews: Drug Discovery 2003, vol. 2, pp. 205-213.
Jung et al., "Discovery of Novel and Potent thiazoloquinazolines as Selective Aurora A and B Kinase Inhibitors," J. Med. Chem. 49:955-970 (2006).
Kamal et al., "Cyclization of 2-(Carbamoyloxy)- and 2-(Sulfamoyloxy)benzoates Mediated by Liver Microsomes," J. Org. Chem. 53:4112-4114 (1988).
Kamal et al., "Enzymatic Cyclization of 2-(Carbamoyloxy)Benzoates, 2-(Sulfamoyloxy)-Benzoates and 2-(Carbamoyloxy)benzopenones with Yeast and Lipase," Heterocycles 29:1391-1397 (1989).
Kanbe et al., "Discovery of thiochroman derivatives bearing a carboxy-containing side chain as orally active pure antiestrogens," Bioorg. & Med. Chem. Lett. 16:4090-4094 (2006).
Kanuma et al., "Lead optimization of 4-(dimethylamino)quinazolines, potent and selective antagonists for the melanin-concentrating hormone receptor 1," Bioorg. & Med. Chem. Lett. 15:3853-3856 (2005).
Keith, "Synthesis and Reduction of some 1H-2,1,3-Benzothiadiazin-4(3H)one 2,2-Dioxides," J. Heterocyclic Chem., 15:1521-1523 (1978).
Khabnadideh et al., "Design, synthesis and evaluation of 2,4-diaminoquinazolines as inhibitors of trypanosomal and leishmanial dihydrofolate reductase," Bioorg. Med. Chem. 13:2637-2649 (2005).
Klinger et al., "Inhibition of Carbonic Anhydrase-II by Sulfamate and Sulfamide Groups: An Investigation Involving Direct Thermodynamic Binding Measurements," J. Med. Chem. 49:3496-3500 (2006).
Kyte et al., "A Simple Method for Displaying the Hydropathic Character of a Protein," J. Mol. Biol. 157:105-132 (1982).
Langer et al., "Chemical and Physical Structure of Polymers as Carriers for Controlled Release of Bioactive Agents: A Review," J. Macromol. Sci. Rev. Macromol Chem. 23:61-126 (1983).
Langer, "New Methods of Drug Delivery," Science 249:1527-1533 (1990).
Lee et al., "Acetonitrile-Mediated Synthesis of 2,4-Dichloroquinoline from 2-Ethynyl-aniline and 2,4-Dichloroquinazoline from Anthranilonitrile," Synlett, 2006 No. 1:65-68 (2006).
Leistner et al., "Eine einfache Synthese von 2-Alhylthio-4-aminothieno[2,3-d]pyrimidinen," Arch. Pharm. (Weinheim) 322:227-230 (1989).
Levy et al, "Inhibition of Calcification of Bioprosthetic Heart Valves by Local Controlled-Release Diphosphonate," Science 228:190-192 (1985).
Li et al., "Human receptors for sweet and umami taste," Proc. Natl. Acad. Sci. USA 99:4692-4696 (2002).
Linkies et al., "Ein neues Verfahren zur Herstellung von 6-Methyl-1,2,3-oxathiazin-4(3H)-on-2,2-dioxid Kaliumsalz (Acesulfam-K)," Synthesis 405-406 (1990).
Liu et al., "Discovery of a new class of 4-anilinopyrimidines as potent c-Jun N-terminal kinase inhibitors: Synthesis and SAR studies," Bioorg. & Med. Chem. Lett. 17:668-672 (2007).
Martinez et al., "Benzothiadiazine Dioxide Dibenzyl Derivatives as Potent Human Cytomegalovirus Inhibitors: Synthesis and Comparative Molecular Field Analysis," J. Med. Chem., 43:3218-3225 (2000).
Meyer, Jr. and Skibo, "Synthesis of Fused [1,2,6]Thiadiazine 1,1-Dioxides as Potential Transition-State Analogue Inhibitors of Xanthine Oxidase and Guanase," J. Med. Chem. 22(8):944-948 (1979).
Naganawa et al., "Further optimization of sulfonamide analogs as EP1 receptor antagonists: Synthesis and evaluation of bioisosteres for the carboxylic acid group," Bioorg. Med. Chem. 14:7121-7137 (2006).
Nie et al., "Distinct Contributions of T1R2 and T1R3 Taste Receptor Subunits to the Detection of Sweet Stimuli," Curr. Biol. 15(21):1948-1952 (2005).
Office Action, U.S. Appl. No. 11/760,592, 13 pages (mailed Jan. 7, 2010).
Office Action, U.S. Appl. No. 11/760,592, 19 pages (mailed Oct. 7, 2010).
Office Action, U.S. Appl. No. 11/760,592, 26 pages (mailed Jan. 16, 2014).
Office Action, U.S. Appl. No. 11/836,074, 11 pages (mailed Sep. 29, 2009).
Office Action, U.S. Appl. No. 11/836,074, 13 pages (mailed Oct. 30, 2008).
Office Action, U.S. Appl. No. 11/836,074, 18 pages (mailed Jun. 10, 2009).
Office Action, U.S. Appl. No. 11/836,074, 18 pages (mailed Jun. 23, 2008).
Office Action, U.S. Appl. No. 11/836,074, 7 pages (mailed Nov. 8, 2010).
Office Action, U.S. Appl. No. 12/663,634, 9 pages (mailed Feb. 6, 2013).
Office Action, U.S. Appl. No. 12/663,634, 8 pages (mailed Apr. 12, 2013).
Office Action, U.S. Appl. No. 12/663,634, 8 pages (mailed Jun. 14, 2013).
Office Action, U.S. Appl. No. 12/663,634, 7 pages (mailed Jul. 19, 2013).
Office Action for U.S. Appl. No. 13/051,586, mailed Jun. 21, 2012.
Office Action for U.S. Appl. No. 13/051,586, mailed Feb. 27, 2013.
Pal et al., "Synthesis and Cyclooxygenase-2 (COX-2) Inhibiting Properties of 1,5-Diarylpyrazoles Possessing N-Substitution on the Sulfonamide (-SO2NH2) Moiety," Letters in Drug Design & Discovery 2:329-340 (2005).
Partial European Search Report, EP appl. No. 12175761.1, 7 pages (Feb. 27, 2013).
Petersen et al., "Synthesis of Heterocycles Containing Two Cytosine or Two Guanine Base-Pairing Sites. Novel Tectons for Self-Assembly," Bioorg. Med Chem. 4:1107-1112 (1996).
Rad-Moghadam et al., "One-pot Three-component Synthesis of 2-Substituted 4-Aminoquinazolines," J. Heterocyclic Chem. 43:913-916 (2006).
Rasmussen et al., "The Electrophilic Addition of Chlorosulfonyl Isocyanate to Ketones. A Convenient Synthesis of Oxazines, Oxathiazines, and Uracils," J. Org. Chem. 38:2114-2115 (1973).
Reddy et al., "An Efficient Synthesis of 3,4-Dihydro-4-Imino-2(1H)-Quinazolinones," Synthetic Commun. 18:525-530 (1988).
Robinson et al., "Sulfonamide Ligands Attained through Opening of Saccharin Derivatives," Eur. J. Org. Chem. 19:4483-4489 (2006).
Rodriguez-Hahn et al., "A Study of the Thorpe-Ziegler Reaction in Very Mild Conditions," Synthetic Commun. 14:967-972 (1984).
Rosowsky and Modest, "Quinazolines. III. Synthesis of 1,3-Diaminobenzo[f]quinazoline and Related Compounds," J. Org. Chem. 31:2607-2613 (1966).
Roy et al., "Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity," J. Org. Chem. 71:382-385 (2006).
Saudek et al., "A Preliminary Trial of the Programmable Implantable Medication System for Insulin Delivery," N. Engl. J Med. 321:574-579 (1989).
Seijas et al., "Microwave enhanced synthesis of 4-aminoquinazolines," Tetrahedron Lett. 41:2215-2217 (2000).
Sharma et al., "Synthesis and QSAR studies on 5-[2-(2-methylprop 1-enyl)-1H benzimidazol-ly1]-4,6-diphenyl-pyrimidin-2-(5H)-thione derivatives as antibacterial agents," Eur. J. Med. Chem. 41:833-840 (2006).
Silve et al., "Delineating a Ca2+ Binding Pocket within the Venus Flytrap Module of the Human Calcium Sensing Receptor," The Journal of Biological Chemistry, Nov. 2005, vol. 280, pp. 37917-37923.
Srivastava et al., "Solid Phase Synthesis of Structurally Diverse Pyrimido[4,5-d] Pyrimidines for the Potential Use in Combinatorial Chemistry," Bioorg. Med. Chem. Lett. 9:965-966 (1999).
Supplementary European Search Report based on EP Application No. 08770047.2, mailed on Sep. 14, 2009.
Tripathi et al., "Reaction of Flavanones with Chlorosulphonyl Isocyanate," Indian J. Chem. Sect. B 26B:1082-1083 (1987).

(56) References Cited

OTHER PUBLICATIONS

Uehling et al., "Biarylaniline Phenethanolamines as Potent and Selective β3 Adrenergic Receptor Agonists," J. Med. Chem. 49:2758-2771 (2006).

Verma et al., "Osmotically Controlled Oral Drug Delivery," Drug Dev. Ind. Pharm. 26:695-708 (2000).

Verschoyle et al., "Pharmacokinetics of Isotretinoin (ISO) in Rats Following Oral Dosing or Aerosol Inhalation," British J. Cancer 80, Suppl. 2:96 Abstract No. P269 (1999).

Vippagunta et al., "Crystalline solids," Adv. Drug Deliv. Rev. 48:3-26 (2001).

Wilson et al., "Synthesis of 5-deazaflavin derivatives and their activation of p53 in cells," Bioorg. & Med. Chem. 15:77-86 (2007).

Wilson, "Traceless Solid-Phase Synthesis of 2,4-Diaminoquinazolines," Org. Lett. 3:585-588 (2000).

Winkler et al., "Synthesis and microbial transformation of β-amino nitriles," Tetrahedron 61:4249-4260 (2005).

Wright, "The Reaction of Sulfamide with α- and β-Diketones. The Preparation of 1,2,5-thiadiazole 1,1-Dioxides and 1,2,6-Thiadiazine 1,1-Dioxides," J. Org. Chem. 29:1905-1909 (1964).

Wright, "The Synthesis of 2,1,3-Benzothiadiazine 2,2-Dioxides and 1,2,3-Benzoxathiazine 2,2-Dioxides," Journal of Organic Chemistry 30(11):3960-3962 (1965).

Written Opinion of the International Searching Authority, 19 pages, PCT Appl. No. PCT/US2008/065650 (mailed Nov. 20, 2008).

Written Opinion of the International Searching Authority, PCT appl. No. PCT/US2013/053666, 6 pages (Dec. 9, 2013).

Xu et al., "Oxidative cyclization of N-alkyl-o-methyl-arenesulfonamides to biologically important saccharin derivatives," Tetrahedron 62:7902-7910 (2006).

Xu et al., "Purine and Pyrididine Nucleotides Inhibit a Noninactivating K1 Current and Depolarize Adrenal Cortical Cells through a G Protein-coupled Receptor," Molecular Pharmacology, 1999, vol. 55, pp. 364-376.

Yamada et al., "Discovery of Novel and Potent Small-Molecule inhibitors of NO and Cytokine Production as Antisepsis Agents: Synthesis and Biological Activity of Alkyl 6-(N-Substituted sulfamoyl)cyclohex-1-ene-1-carboxylate," J. Med. Chem. 48:7457-7467 (2005).

Yoshizawa et al., "Efficient solvent-free Thrope reaction," Green Chem. 4:68-70 (2002).

Zunszain et al., "Search for the pharmacophore in prazosin for Transport-P," Bioorg. & Med. Chem. 13:3681-3689 (2005).

SWEET FLAVOR MODIFIER

CROSS-REFERENCE TO RELATED APPLICATIONS

This application claims the benefit of priority to U.S. Provisional Application No. 61/766,652, filed on Feb. 19, 2013, the contents of which are hereby incorporated by reference herein in their entireties for all purposes.

FIELD OF THE INVENTION

The invention relates to compounds suitable for modifying receptors and their ligands associated with chemosensory or chemosensory related sensation or reaction.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami (the taste of monosodium glutamate, a.k.a. savory taste).

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. Also, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

It has been reported that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Certain compounds have been reported to be modulators of the chemosensory receptors in T1R family and/or their ligands and are described in the four patent applications listed below.

(1) U.S. patent application Ser. No. 11/760,592, entitled "Modulation of Chemosensory Receptors and Ligands Associated Therewith", filed Jun. 8, 2007; (2) U.S. Pat. No. 7,928,111, entitled "Modulation of Chemosensory Receptors and Ligands Associated Therewith", issued Apr. 19, 2011; and (3) International Application No. PCT/US2008/065650, entitled "Modulation of Chemosensory Receptors and Ligands Associated Therewith", filed Jun. 3, 2008. The content of these applications are herein incorporated by reference in their entirety for all purposes.

There is a need in the art to develop novel and inventive compounds suitable for modifying receptors and/or their ligands associated with chemosensory or chemosensory related sensation or reaction.

SUMMARY OF THE INVENTION

In one embodiment, the present invention provides a compound having structural Formula (I):

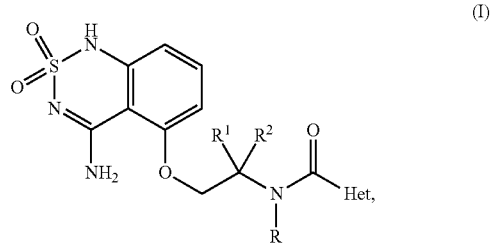

(I)

or a salt or solvate thereof; wherein, $R^1$ and $R^2$ are independently C1 to C4 alkyl; or alternatively, $R^1$ and $R^2$, together with the carbon atom to which they are attached, form a C3 to C7 cycloalkyl;

R is hydrogen or C1 to C6 alkyl; and Het is heteroaryl or substituted heteroaryl.

In another embodiment, the present invention provides an ingestible composition comprising a compound of the present invention; and optionally an ingestibly acceptable excipient.

In another embodiment, the present invention provides a method of increasing the sweet taste of an ingestible composition comprising contacting the ingestible composition thereof with a compound of the present invention to form a modified ingestible composition. In the method, the present compound can be a chemosensory receptor modifier, a chemosensory receptor ligand modifier, or both, i.e., a partial chemosensory receptor modifier and partial chemosensory receptor ligand modifier. For example, the present compound can be a sweet receptor agonist, or a sweet enhancer, or a partial sweet receptor agonist and partial sweet enhancer.

In another embodiment, the present invention provides a sweet enhancing composition, comprising a compound of the present invention in an amount effective to provide sweetening in combination with a first amount of sweetener, wherein the sweetening is more than the sweetening provided by the first amount of sweetener without the compound.

In another embodiment, the present invention provides a flavoring concentrate formulation comprising i) as flavor modifying ingredient, a compound of the present invention; ii) a carrier; and iii) optionally at least one adjuvant.

DETAILED DESCRIPTION OF THE INVENTION

These and other embodiments, advantages, and features of the present invention are provided in the sections below. Unless defined otherwise, all technical and scientific terms used herein have the same meaning as commonly understood by one of ordinary skill in the art to which this invention belongs.

Definitions

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl; prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined herein below. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. "Alkoxy," by itself or as part of another substituent, refers to a radical of the formula —O—$R^{199}$, where $R^{199}$ is alkyl or substituted alkyl as defined herein.

"Acyl" by itself or as part of another substituent refers to a radical —$C(O)R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl), i.e., 6- to 20-membered aryl ring. In other embodiments, an aryl group comprises from 6 to 15 carbon atoms ($C_6$-$C_{15}$ aryl), i.e., 6- to 15-membered aryl ring. In still other embodiments, an aryl group comprises from 6 to 15 carbon atoms ($C_6$-$C_{10}$ aryl), i.e., 6- to 10-membered aryl ring.

"Arylalkyl" or "aralkyl" by itself or as part of another substituent, refers to an acyclic alkyl group in which one of the hydrogen atoms bonded to a carbon atom, typically a terminal or $sp^3$ carbon atom, is replaced with an aryl group as, as defined herein. That is, an arylalkyl or aralkyl group is composed of an aryl group connected to an alkylene group which is further attached to other portion of a molecule. The alkylene group in the arylalkyl or aralkyl group can be an alkylene having 1 to 12 carbon atoms, or 1 to 6 carbon atoms, or 1 to 3 carbon atoms. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is $(C_6-C_{20})$ aryl. In other embodiments, an arylalkyl group is $(C_6-C_{20})$ arylalkyl, e.g., the alkanyl, alkenyl or alkynyl moiety of the arylalkyl group is $(C_1-C_8)$ alkyl and the aryl moiety is $(C_6-C_{12})$ aryl. In still other embodiments, an arylalkyl group is $(C_6-C_{15})$ arylalkyl, e.g., the alkanyl, alkenyl or alkynyl moiety of the arylalkyl group is $(C_1-C_5)$ alkyl and the aryl moiety is $(C_6-C_{10})$ aryl.

"Cycloalkyl," or "Carbocyclyl," by itself or as part of another substituent, refers to a saturated or unsaturated cyclic alkyl radical, as defined herein. Similarly, "Cycloalkylene," or "Carbocyclylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3-C_{10}$ cycloalkyl). In other embodiments, the cycloalkyl group comprises from 3 to 7 ring atoms ($C_3-C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," or "Heterocyclylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1-C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom. In one embodiment, heterocyclyl includes "azacyclyl" which denotes a heterocycle having one or more nitrogen atoms in the ring. An azacyclyl may also contain additional other heteroatom(s), such as oxygen and sulfur. An azacyclyl may be a four, five, six, seven, or eight-membered ring having one or more nitrogen atoms, such as azetidine, imidazolidine, morpholine, piperazine, piperidine, pyrazolidine, pyrrolidone, diazepane, azepane, diazocane, and azocane.

"Compounds" refers to compounds encompassed by structural formulae disclosed herein, such as (I), (Ia), and (Ib) and includes any subgeneric and specific compounds within these formulae whose structures are disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. That is, a heteroarylalkyl group is composed of a heteroaryl group connected to an alkylene group which is further attached to other portion of a molecule. The alkylene group in the heteroarylalkyl group can be an alkylene having 1 to 12 carbon atoms, or 1 to 6 carbon atoms, or 1 to 3 carbon atoms. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanylene, alkenylene or alkynylene moiety of the heteroarylalkyl is $(C_1-C_6)$ alkylene and the heteroaryl moiety is a 5-15-membered heteroaryl. In other embodiments, the heteroarylalkyl is a 6-13 membered heteroarylalkyl, e.g., the alkanylene, alkenylene or alkynylene moiety is $(C_1-C_3)$ alkylene and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N=O$ or $R_3N \rightarrow O$).

"Substituted," when used to modify a specified group or radical, means that one or more hydrogen atoms of the specified group or radical are each, independently of one another, replaced with the same or different substituent(s). The term "optionally substituted" means substitued or nonsubstituted. For example, an optionally substituted azacyclic ring means the azacyclic ring can be substituted or nonsubstituted. Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-$C(O)OR^b$, -alkylene-$C(O)NR^bR^b$, and —$CH_2$—$CH_2$—$C(O)$—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$—$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$, $R^b$ and $R^c$ are as previously defined. Substituent groups from the above lists useful for substituting other specified groups or atoms will be apparent to those of skill in the art.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

"Vehicle" refers to a diluent, adjuvant, excipient or carrier with which a compound is administered.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

According to the present invention, a chemosensory receptor can be any receptor associated with chemosensory sensation or chemosensory ligand triggered signal transduction, e.g., via taste receptors or taste related receptors expressed in taste bud or internal organs of the body, such as gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

An "enhancer" herein refers to a compound, or an ingestibly acceptable salt or solvate thereof, that modulates (increases) the activation of a particular receptor, preferably the chemosensory, e.g., T1R2/T1R3 receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto. Some enhancers, at its ligand enhancing concentration, do not result in activation of the particular receptor by themselves. That is, the ligand enhancing concentrations of these enhancers are concentration levels of the enhancers that increase or enhance the activation of a particular receptor by a ligand without substantially activating the particular receptor by the enhancers themselves. In some embodiments, certain enhancers, when used at a concentration higher than the ligand enhancing concentration, can also activate a particular receptor by themselves in addition to modulating (e.g., increase or enhancement) the activation of the receptor. For example, certain enhancers, when used at a concentration higher than the ligand enhancing concentration, can be sweeteners (i.e., sweet flavoring agent/entity) as well. In other embodiments, certain enhancers can activate a particular receptor by themselves in addition to modulating (e.g., increase or enhancement) the activation of the receptor simultaneously at the same concentration. In other words, certain enhancers are also sweeteners (i.e., sweet flavoring agent/entity) at the same time.

A "flavor" herein refers to the perception of taste in a subject, which include sweet, sour, salty, bitter and umami. The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "flavor modifier" or "flavor modifying agent" herein refers to a compound or the ingestibly acceptable salt or solvate thereof that modulates, including enhancing or potentiating, and/or inducing, the tastes of a flavoring agent in an animal or a human.

A "flavor enhancer" herein refers to a compound or ingestibly acceptable salt thereof that enhances and/or multiplies the tastes of a flavoring agent, or an ingestible composition comprising the flavoring agent.

A "sweet flavor" refers to the sweet taste typically induced by sugar, such as fructose, in an animal or a human.

A "sweet flavoring agent", "sweet flavor entity", "sweetener", or "sweet compound" herein refers to a compound or ingestibly acceptable salt thereof that elicits a detectable sweet flavor in a subject, e.g., fructose or a compound that activates a T1R2/T1R3 receptor in vitro. The subject may be a human or an animal.

A "sweet flavor modifier" or "sweet flavor modifying agent" herein refers to a compound or ingestibly acceptable salt or solvate thereof that modulates, including enhancing or potentiating, inducing, or blocking, the sweet taste of a sweet flavoring agents in an animal or a human. The sweet flavor modifier includes both sweet flavor enhancer and sweet flavoring agent.

A "sweet flavor enhancer" or "sweet flavor enhancing agent" herein refers to an enhancer of a sweet flavor wherein the term enhancer is the same as defined above.

A "sweet receptor activating compound" or "sweet receptor agonist" herein refers to a compound that activates a sweet receptor, such as a T1R2/T1R3 receptor. One example of a sweet receptor activating compound is a sweetener, such as fructose.

A "sweet receptor modulating compound" herein refers to a compound that modulates (activates, block, or enhances/reduces activation of) a sweet receptor such as a T1R2/T1R3 receptor.

A "sweet receptor enhancing compound" herein refers to a compound that enhances or potentiates the effect of a sweet receptor activating compound, e.g., fructose.

The present sweet receptor enhancing compounds or sweet flavor enhancers, at its ligand enhancing concentration of use, may or may not result in activation of the particular receptor by themselves. Some of the sweet receptor enhancing compounds or sweet flavor enhancers, can also activate a particular receptor by themselves in addition to modulating (increase) the activation of the receptor. For example, some of the sweet receptor enhancing compounds or sweet flavor enhancerscan also activate a sweet receptor, such as a T1R2/T1R3 receptor, acting as the receptor agonists.

A "sweet flavor modulating amount" herein refers to an amount of a compound of Formula (I) that is sufficient to alter (either increase or decrease) sweet taste in an ingestible composition, or a precursor thereof, sufficiently to be perceived by a human subject. In many embodiments of the invention, at least about 0.001 ppm of the present compound would need to be present in order for most human subjects to perceive a modulation of the sweet flavor of an ingestible composition comprising the present compound. A broad range of concentration that would typically be employed in order to economically provide a desirable degree of sweet flavor modulation can be from about 0.001 ppm to 100 ppm, or a narrow range from about 0.1 ppm to about 10 ppm. Alternative ranges of sweet flavor modulating amounts can be from about 0.01 ppm to about 30 ppm, from about 0.05 ppm to about 15 ppm, from about 0.1 ppm to about 5 ppm, or from about 0.1 ppm to about 3 ppm.

A "sweet flavor enhancing amount" herein refers to an amount of a compound that is sufficient to enhance the taste of flavoring agents, e.g., fructose, in a ingestible composition, as perceived by an animal or a human. A broad range of a sweet flavor enhancing amount can be from about 0.001 ppm to 100 ppm, or a narrow range from about 0.1 ppm to about 10 ppm. Alternative ranges of sweet flavor enhancing amounts can be from about 0.01 ppm to about 30 ppm, from about 0.05 ppm to about 15 ppm, from about 0.1 ppm to about 5 ppm, or from about 0.1 ppm to about 3 ppm. In some embodiments, sweet flavor enhancing amount is the amout corresponding to ligand enhancing concentration(s) of a sweet flavor enhancer of the present invention.

A "sweet receptor modulating amount" herein refers to an amount of a compound that is sufficient to modulate (activate, enhance or block) a sweet taste receptor protein. In many embodiments of the invention, a sweet receptor modulating amount is at least about 10 nM, or at least about 100 nM (i.e. about 0.1 μM), or at least about 1 μM, or at least about 10 μM. A "T1R2/T1R3 receptor modulating or activating amount" is an amount of compound that is sufficient to modulate or activate a T1R2/T1R3 receptor. A "sweet receptor" is a taste receptor that can be modulated by a sweet compound. Preferably a sweet receptor is a G protein coupled receptor, and more preferably the sweet receptor is a T1R2/T1R3 receptor.

Compounds

In one embodiment, the present invention provides a compound having structural Formula (I):

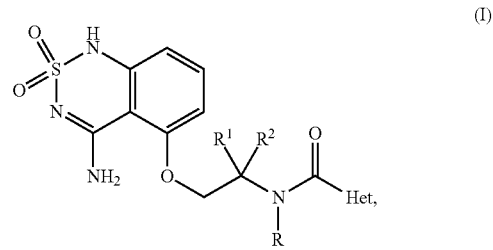

or a salt or solvate thereof; wherein, $R^1$ and $R^2$ are independently C1 to C4 alkyl; or alternatively, $R^1$ and $R^2$, together with the carbon atom to which they are attached, form a C3 to C7 cycloalkyl;

R is hydrogen or C1 to C6 alkyl; and Het is heteroaryl or substituted heteroaryl.

In one embodiment of Formula (I), R is hydrogen.

In one embodiment of Formula (I), $R^1$ and $R^2$ are both methyl, ethyl, or propyl.

In one embodiment of Formula (I), wherein $R^1$ and $R^2$, together with the carbon atom to which they are attached, form cyclopropyl, cyclobutyl, cylclopentyl, or cyclohexyl.

In one embodiment of Formula (I), wherein Het is an optionally substituted monocyclic five or six-membered heteroaryl containing one or more heteroatoms selected from the group of N, O, and S.

In one embodiment of Formula (I), wherein Het is an optionally substituted pyridine, pyrimidine, N-oxide pyridine, or N-oxide pyrimidine.

In one embodiment of Formula (I), wherein Het is an optionally substituted bicyclic ten to twelve-membered heteroaryl containing one or more heteroatoms selected from the group of N, O, and S.

In one embodiment of Formula (I), the compound is represented by structural Formula (Ia):

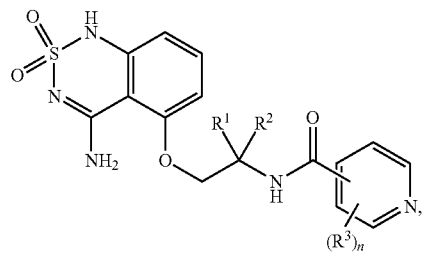
(Ia)

wherein, n is 0, 1, 2, or 3; and $R^3$ is halo, cyano, hydroxyl, amine, alkoxy, alkylamine, acyl, acylamine, amide, sulfonamide, ester, alkyl, substituted alkyl, heteroalkyl, substituted heteroalkyl, aryl, substituted aryl, heteroaryl, substituted heteroaryl, carbocyclyl, or substituted carbocyclyl.

In one embodiment of Formula (Ia), $R^1$ and $R^2$ are both methyl, ethyl, or propyl.

In one embodiment of Formula (Ia), $R^1$ and $R^2$, together with the carbon atom to which they are attached, form cyclopropyl, cyclobutyl, cylclopentyl, or cyclohexyl.

In one embodiment of Formula (Ia), the compound is represented by structural Formula (Ib):

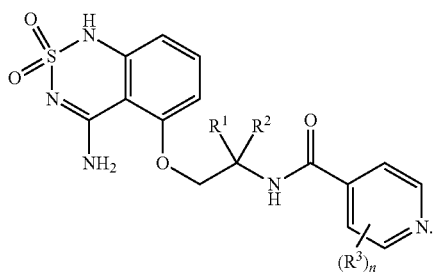
(Ib)

In certain specific embodiments, the compounds of the present invention are selected from the group consisting of

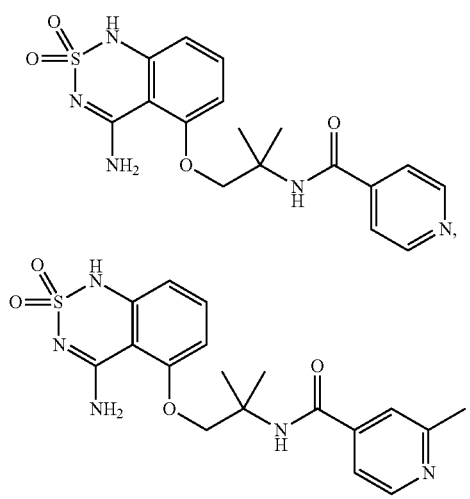

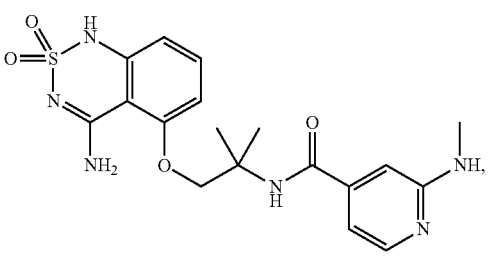

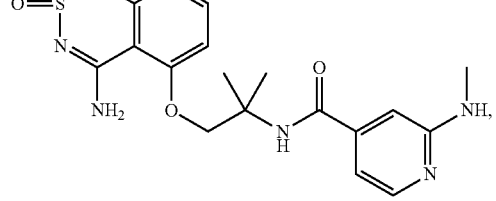

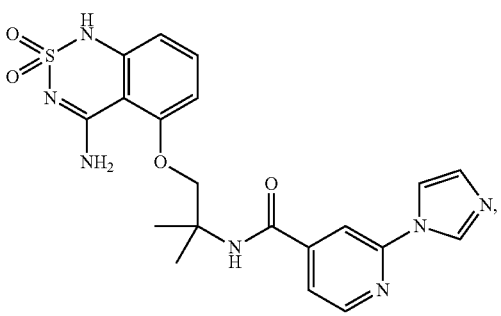

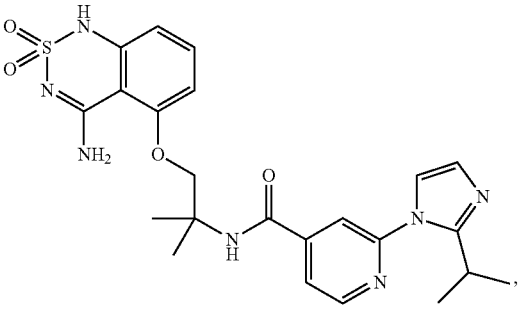

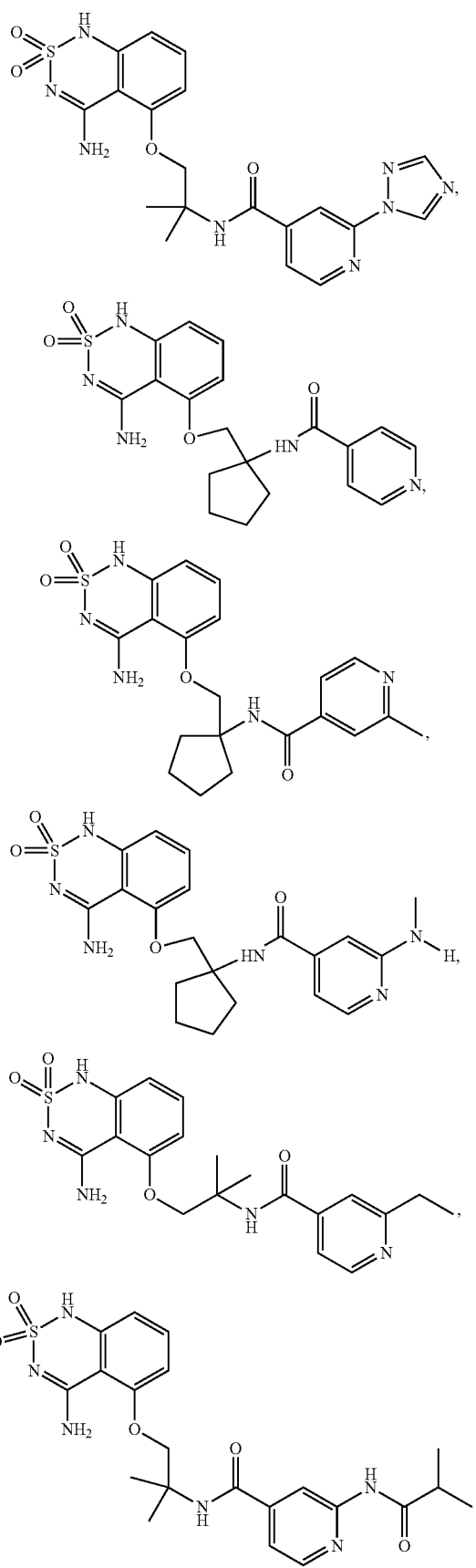
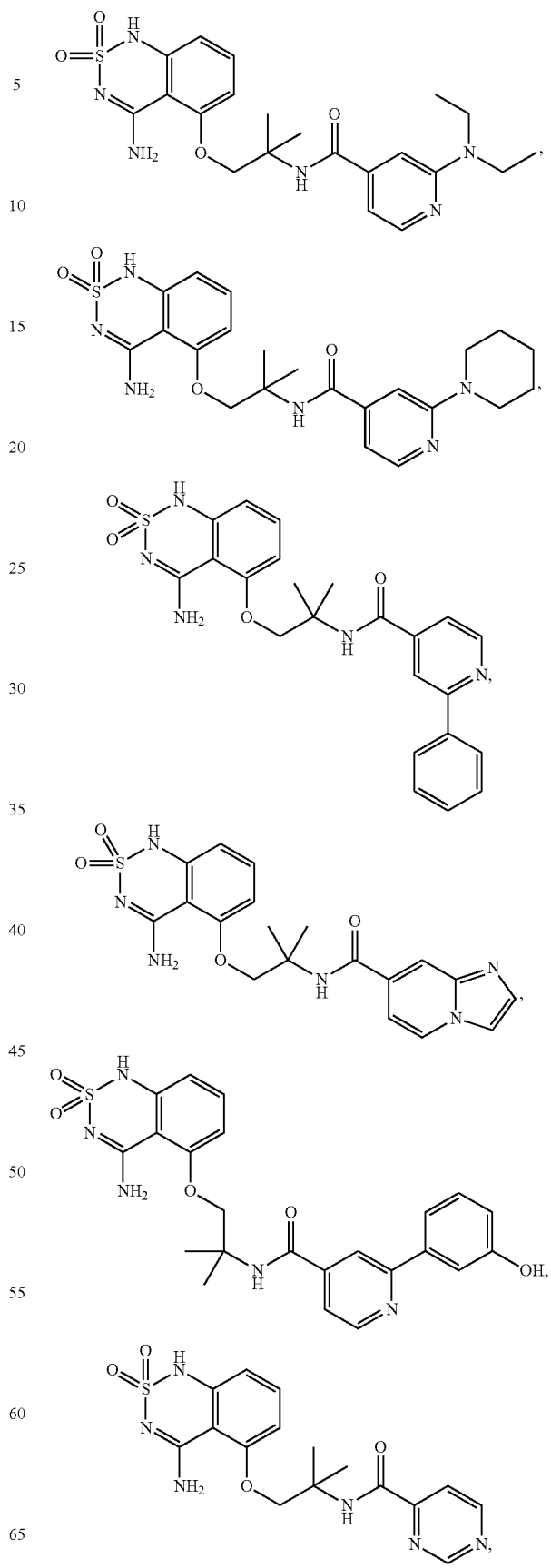

17
-continued
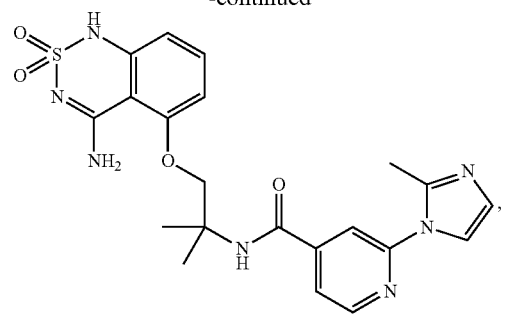
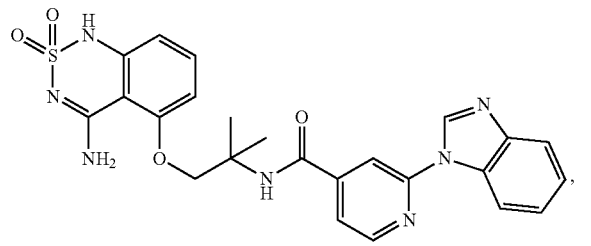
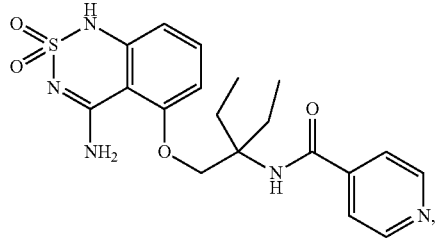
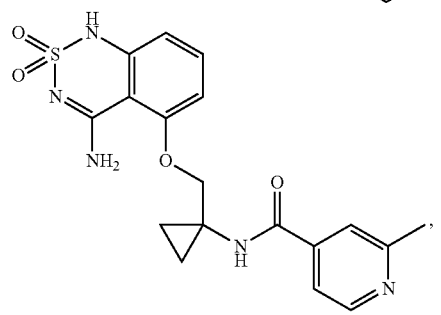
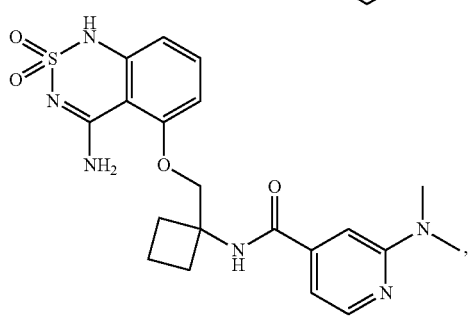
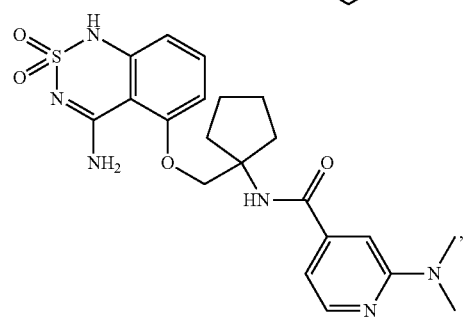
18
-continued
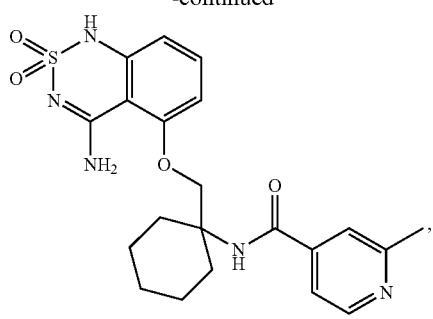
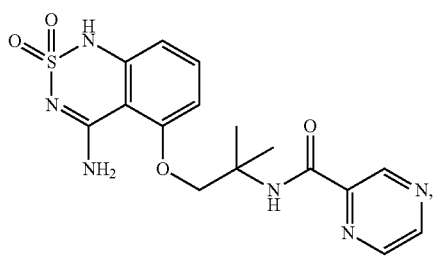
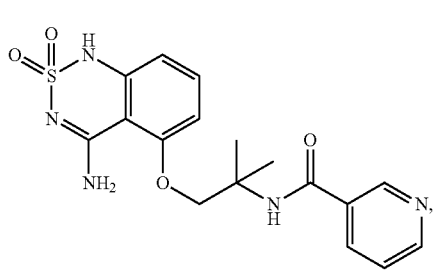
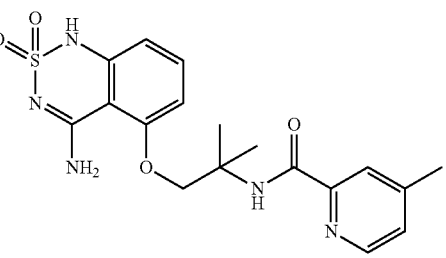
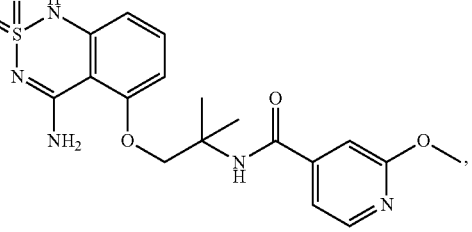
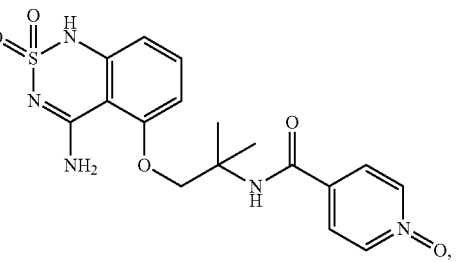

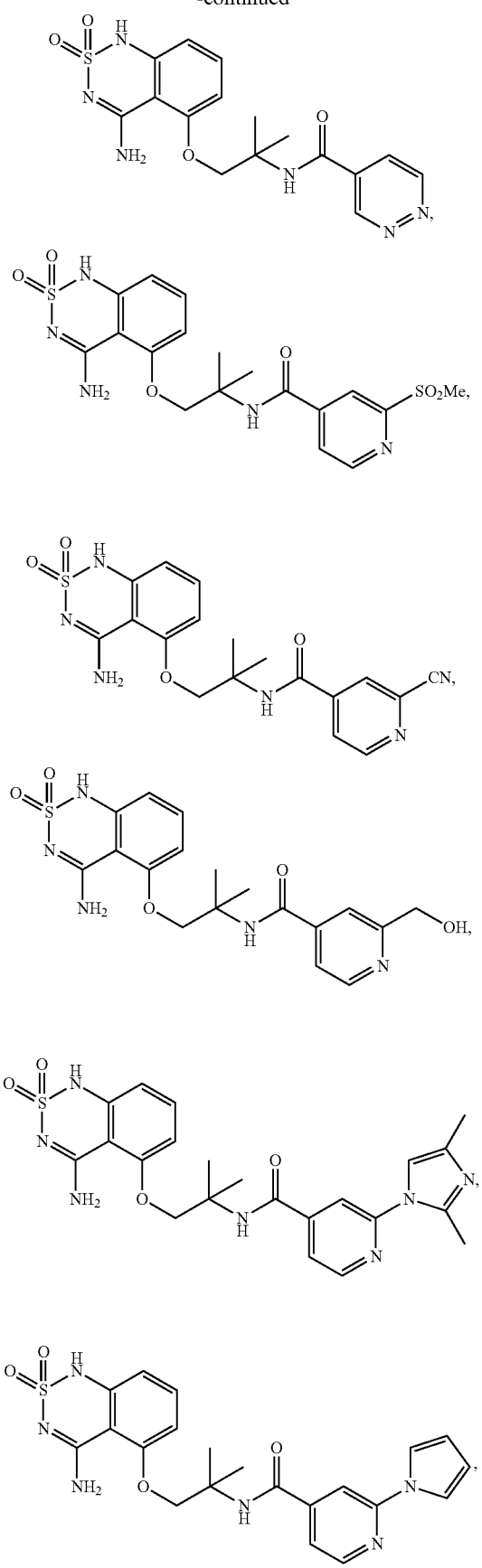

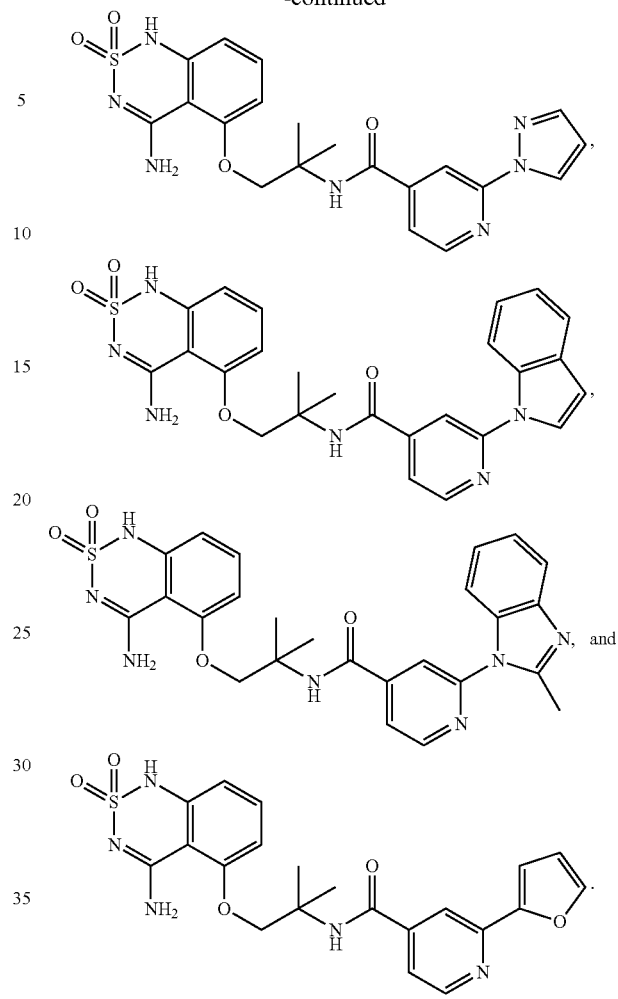

Compositions

The present compounds can be used for one or more methods of the present invention, e.g., modifying receptors and their ligands associated with chemosensory or chemosensory related sensation or reaction. According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g., gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ. In general, the compounds of the present invention, individually or in combination, can be provided in a composition, such as, e.g., an ingestible composition. In one embodiment, the present compound can impart a more sugar-like temporal profile and/or flavor profile to a sweetener composition by combining one or more present compound with one or more sweetener in the sweetener composition. In another embodiment, the present compound can increase or enhance the sweet taste of a composition by contacting the composition thereof with one or more present compound to form a modified composition. In another embodiment, the present compound can be in a composition that modulates the sweet receptors and/or their ligands expressed in the body other than in the taste buds.

The compounds of Formula (I), (Ia), (Ib), and its various subgenuses and species, and their salts and/or solvates, should preferably be comestibly acceptable, e.g., deemed suitable for consumption in food or drink from the perspective of giving unmodified comestible compositions an improved and/or pleasing sweet taste, and would not be significantly toxic or causes unpleasant or undesirable pharmacological or toxicological effects on an animal or human at the typical concentrations they are employed as flavoring agents for the comestible compositions.

One of the methods of demonstrating that a flavorant compound is comestibly acceptable is to have the compound tested and/or evaluated by an Expert Panel of the Flavor and Extract Manufacturers Association (FEMA) and declared as to be "Generally Recognized As Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5), pgs 46-59, May 2003, the entire contents of which are hereby incorporated herein by reference. In addition to the FEMA expert panel, an independent, qualified panel of experts in pertinent scientific disciplines may be formed by the manufacturer to evaluate the safety of a specific compound for GRAS status. This process is known as a "self determination of GRAS status." Another method of demonstrating that a flavorant compound is comestibly acceptable is to obtain favorable review by the WHO/FAO Joint Expert Committee on Food Additives, or JECFA. There are also other evaluation methods, such as independent review by the regulatory agency, which are generally known to those of ordinary skill in the food product preparation arts.

In one embodiment, the compounds of the present invention can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment, the present compounds can enhance the sweetness of a sweetener under a broad range of pH, e.g., from lower pH to neutral pH. The lower and neutral pH includes, but is not limited to, a pH from about 2.5 to about 8.5; from about 2.5 to about 8.0; from about 2.8 to about 7.5; from about 3.0 to about 7, and from about 3.5 to about 7. In certain embodiments, the present compounds can enhance the perceived sweetness of a fixed concentration of a sweetener in taste tests at a compound concentration of about 50 µM, 40 µM, 30 µM, 20 µM, or 10 µM at both low to neutral pH value. In certain embodiments, the enhancement factor of the present compounds at the lower pH is substantially similar to the enhancement factor of the compounds at neutral pH. Furthermore, in some embodiments, the present compounds demonstrate enhanced photostability. That is, when exposed to a light source, the presnet compounds have stability and less prone to degradation. Such photostability and consistent sweet enhancing property under a broad range of pH render the present compounds good candidates for a broad use in a wide variety of foods and beverages.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

In one embodiment, the present compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In another embodiment, the present compounds are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of known sweeteners, e.g., so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the ingestible composition will of course depend on many variables, including the specific type of the ingestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the present compounds is for modulating (inducing, enhancing or inhibiting) the sweet taste or other taste properties of other natural or synthetic sweet tastants, and ingestable compositions made therefrom. In one embodiment, the compounds of the present invention is used or provided in its ligand enhancing concentration(s). For example, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In one embodiment, the present invention provides a sweet enhancing composition. The sweet enhancing composition comprises a compound of the present invention in an amount effective to provide sweetening, e.g., sweet flavor enhancing amount in combination with a first amount of sweetener, wherein the sweetening is more than the sweetening provided by the first amount of sweetener without the compound.

In one embodiment, the present invention provides an ingestible composition which comprises the sweet enhancing composition of the present invention. In certain embodiments, the present ingestible composition is in the form of a food or beverage product, a pharmaceutical composition, a nutritional product, a dietary supplement, over-the-counter medication, or oral care product.

In one embodiment, the present invention provides a sweetener replacement composition which comprises one or more compounds of the present invention in an amount effective to provide sweetening, e.g., at a concentration higher than their ligand enhancing concentration in the absence of a sweetener, e.g., sucrose other than the present compound(s).

According to another aspect of the invention, the compounds of the present invention are provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacture in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) as flavor modifying ingredient, a compound of the present invention; ii) a carrier; and iii) optionally at least one adjuvant. The term "as flavor modifying ingredient" denotes that the compound of the present invention acts as a flavoring agent or a flavor modifying agent (such as a flavor enhancer) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. The present flavoring concentrate formulation can be carbonated or non-carbonated.

The flavoring concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions oïMethoden der Organischen Chemie (Houben-Weyl), and the like. Many general methods for preparation of starting materials comprising variously substituted heterocyclic, hetereoaryl, and aryl rings (the precursors of Ar, hAr$^1$, and/or hAr$^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3$^r$ Ed., John Wiley & Sons (1999).

Some exemplary synthetic methods useful for preparing the present compounds or the intermediates thereof can be found in WO 2010/014666, entitled "Processes and Intermediates for Making Sweet Taste Enhancers" and published on Feb. 4, 2010.

EXAMPLES

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

Example 1

N-(1-(4-amino-2,2-dioxide-1H-benzo[c][1,2,6]thiadiazin-5-yloxy)-2-methylpropan-2-yl)isonicotinamide

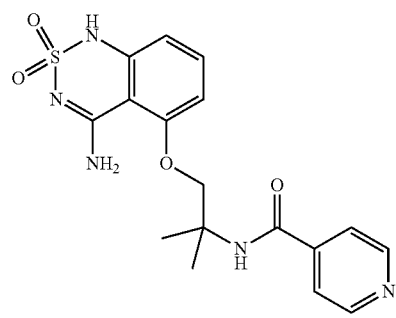 [SMILES: CC(C)(COc1cccc2c1C(N)=NS(=O)(=O)N2)NC(=O)c1ccncc1]

To a stirred suspension of 5-(2-amino-2-methylpropoxy)-1H-benzo[c][1,2,6]thiadiazin-4-amine-2,2-dioxide hydrochloride 5-(3-amino-3-methylbutyl)-1H-benzo[c][1,2,6]thiadiazin-4-amine-2,2-dioxide hydrochloride (962 mg, 3 mmol, Example 1a) in DMF (25 mL) was added triethylamine (0.834 mL, 6 mmol). After being stirred at room temperature for 10 min., a mixture of isonicotinic acid (369 mg, 3 mmol), EDCI (575 mg, 3 mmol) and HOBt (405 mg, 3 mmol) in 15 ml of DMF was added and the reaction mixture

Example 1a 1-((4-amino-2,2-dioxido-1H-benzo[c][1,2,6]thiadiazin-5-yl)oxy)-2-methylpropan-2-aminium chloride

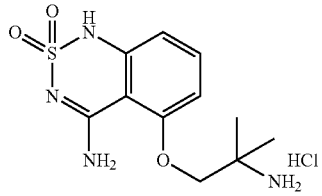 [SMILES: CC(C)(N)COc1cccc2c1C(N)=NS(=O)(=O)N2 ; Cl]

To a solution of tert-butyl(1-((4-amino-2,2-dioxido-1H-benzo[c][1,2,6]thiadiazin-5-yl)oxy)-2-methylpropan-2-yl-carbamate (114 g, 296 mmol) in ethanol (1 L), cooled to 0° C., was added HCl (4.0 M in dioxane, 370 mL, 1480 mmol). The mixture was stirred at 0° C. for 3 hours under nitrogen, and then allowed to warm to room temperature. The mixture was concentrated and the residue was suspended in diethyl ether (2 L) and refluxed for 1 hour. The mixture was cooled to room temperature and the solid was collected by vacuum filtration and dried under high vacuum to afford 1-((4-amino-2,2-dioxido-1H-benzo[c][1,2,6]thiadiazin-5-yl)oxy)-2-methylpropan-2-aminium chloride as a white solid (94 g, 100%). $^1$H NMR (DMSO-$d_6$), 400 MHz: δ 1.37 (s, 6H), 4.12 (s, 2H), 6.70 (d, J=8.0 Hz, 1H), 6.85 (d, J=8.0 Hz, 1H), 7.48 (t, J=8.0 Hz, 1H), 7.65 (s, 1H), 8.43 (br s, 3H), 10.9 (br s, 1H). MS 285 (MH$^+$).

Example 1b

Tert-butyl(1-((4-amino-2,2-dioxido-1H-benzo[c][1,2,6]thiadiazin-5-yl)oxy)-2-methylpropan-2-yl-carbamate To a solution of tert-butyl (1-2-cyano-3-(sulfamoylamino) penoxy)-2-methylpropan-2-yl)carbamate (189 g, 492 mmol) in ethanol (1.5 L) was added solid NaOH (74 g, 1968 mmol), and the reaction was stirred at 115° C. for 13 hours under nitrogen. Upon completion, the mixture was cooled to 0° C. and neutralized with acetic acid. The precipitate was collected by vacuum filtration and dried under high vacuum to afford tert-butyl(1-((4-amino-2,2-dioxido-1H-benzo[c][1,2,6]thiadiazin-5-yl)oxy)-2-methylpropan-2-yl-carbamate as a white solid (114 g, 61%). $^1$H NMR (DMSO-$d_6$), 400 MHz: δ 1.27 (s, 6H), 1.34 (s, 9H), 4.16 (s, 2H), 6.55 (d, J=8.0 Hz, 1H), 6.63 (d, J=8.0 Hz, 1H), 6.94 (br s, 1H), 7.37 (t, J=8.0 Hz, 1H), 7.75 (br s, 1H), 8.17 (br s, 1H), 10.8 (br s, 1H). MS 285 (MH$^+$).

was then stirred at room temperature overnight. The resulting solution was concentrated and purified by HPLC, and then the product was recrystallized from ethanol/water, after dry to give the title compound as a off white powder (760 mg) in 65% yield. M.p.: 235-238° C. $^1$H NMR (400 MHz, DMSO-$d_6$) δ 1.47 (s, 6H), 4.37 (s, 2H), 6.61 (d, J=7.6 Hz, 1H), 6.78 (d, J=7.6 Hz, 1H), 7.45 (t, J=8.4 Hz, 1H), 7.65 (d, J=6 Hz, 2H), 7.83 (s, 1H), 8.48 (s, 2H), 8.67 (d, J=6 Hz, 2H), 10.98 (s, 1H). MS 390 (MH$^+$).

Example 1c

Tert-butyl (1-2-cyano-3-(sulfamoylamino)penoxy)-2-methylpropan-2-yl)carbamate

To a solution of tert-butyl(1-(3-amino-2-cyanophenoxy)-2-methylpropan-2-yl)carbamate (150 g, 492 mmol) in THF (1.8 L) was added lutidine (86 mL, 738 mmol). The mixture was cooled to −45° C. and sulfamoyl chloride (71 g, 616 mmol), dissolved in dichloromethane (400 mL), was added. After 10 min, the reaction was warmed to room temperature and stirred for 2 hours. Upon completion, solid NaHCO$_3$ (123 g, 1476 mmol) was added, and the mixture was stirred for 30 minutes, followed by concentration. The residue was diluted with ethyl acetate (1.8 L), washed with water (1 L), dried over anhydrous Na$_2$SO$_4$, filtered and concentrated in vacuo to provide tert-butyl (1-2-cyano-3-(sulfamoylamino)penoxy)-2-methylpropan-2-yl)carbamate as a clear oil, which was used immediately in the next step. MS 285 (MH$^+$).

Example 1d

Tert-butyl(1-(3-amino-2-cyanophenoxy)-2-methylpropan-2-yl)carbamate

To a solution of tert-butyl(1-(2-cyano-3-nitrophenoxy)-2-methylpropan-2-yl)carbamate (45 g, 134 mmol) in ethyl acetate (200 mL) and ethanol (100 mL) was added 10% palladium on carbon (4.5 g). The reaction was stirred under H2 at 40 psi, and upon completion, the mixture was filtered through a pad of celite, and the filtrate was concentrated in vacuo to provide tert-butyl(1-(3-amino-2-cyanophenoxy)-2-methylpropan-2-yl)carbamate as a white solid (41 g, 100%). $^1$H NMR (DMSO-$d_6$), 400 MHz: δ 1.26 (s, 6H), 1.34 (s, 9H), 4.00 (s, 2H), 5.96 (br s, 2H), 6.15 (d, J=8.0 Hz, 1H), 6.31 (d, J=8.0 Hz, 1H), 6.63 (br s, 1H), 7.14 (t, J=8.0 Hz, 1H). MS 206 (MH$^+$).

Example 1f

Tert-butyl(1-(2-cyano-3-nitrophenoxy)-2-methylpropan-2-yl)carbamate

To a solution of 2-amino-2-methylpropan-1-ol (48 mL, 500 mmol) in THF (2 L) at −30° C., was added NaH (60% dispersion in oil, 22 g, 550 mmol) in one portion. The mixture was stirred for 10 minutes under nitrogen, and then warmed to room temperature. After 2 hours, the mixture was cooled −60° C. and 2,6-dinitrobenznitrile (97 g, 500 mmol) was added. After 10 min, the solution was warmed to room temperature, and stirred for 13 h, then cooled back down to −30° C. and di-tert-butyl dicarbonate (131 g, 600 mmol) dissolved in THF (100 mL) was added. The reaction was stirred for 10 minutes at −30° C., then at room temperature for 13 hours. Upon completion, the reaction was neutralized with 10% citric acid and concentrated. The residue was diluted with ethyl acetate (1 L), washed with saturated aq. NaCl solution, dried over anhydrous Na$_2$SO$_4$ and filtered. The solvent was removed by in vacuo to obtain tert-butyl(1-(2-cyano-3-nitrophenoxy)-2-methylpropan-2-yl)carbamate as a beige solid (167 g, 100%). $^1$H NMR (DMSO-$d_6$), 400 MHz: δ 1.30 (s, 6H), 1.32 (s, 9H), 4.28 (s, 2H), 6.76 (br s, 1H), 7.68 (d, J=4.0 Hz, 1H), 7.85 (t, J=8.0 Hz, 1H), 7.91 (d, J=8.0 Hz, 1H). MS 336 (MH$^+$).

Alternate Synthesis of Example 1

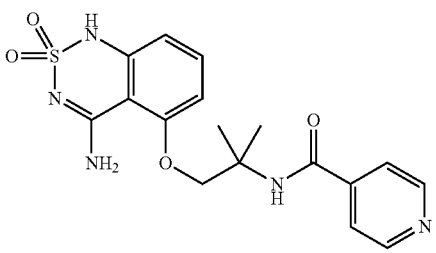 [SMILES: CC(C)(COc1cccc2c1C(N)=NS(=O)(=O)N2)NC(=O)c1ccncc1]

To a stirred suspension of N-(1-(2-cyano-3-(sulfamoylamino)phenoxy)-2-methylpropan-2-yl)isonicotinamide (, 12.2 g, 31.2 mmol) in EtOH (80 mL) was added NaOH solution (2.0 N, 40 mL, 80 mmol) at room temperature. The reaction mixture was then refluxed for 3 hrs until the reaction was complete checked by LC/MS. The reaction solution was cooled to 0° C. and neutralized carefully with 2N HCl water solution, the precipitate was collected by filtration, and then re-crystallized from EtOH/H$_2$O, dried in vacuum oven at 55° C. to give the title compound as a white solid (7.91 g) in 65% yield. M.p.: 235-238° C. $^1$H NMR (400 MHz, DMSO-d$_6$) δ 1.47 (s, 6H), 4.37 (s, 2H), 6.61 (d, J=7.6 Hz, 1H), 6.78 (d, J=7.6 Hz, 1H), 7.45 (t, J=8.4 Hz, 1H), 7.65 (d, J=6 Hz, 2H), 7.83 (s, 1H), 8.48 (s, 2H), 8.67 (d, J=6 Hz, 2H), 10.98 (s, 1H). MS 390 (MH$^{-1}$).

Synthesis of N-(1-(2-cyano-3-(sulfamoylamino)phenoxy)-2-methylpropan-2-yl)isonicotinamide To a solution of N-(1-(3-amino-2-cyanophenoxy)-2-methylpropan-2-yl)isonicotinamide (10.76 g, 34.67 mmol) in DMA (35 mL) was added sulfamoyl chloride (7.98 g, 69.34 mmol) at room temperature under nitrogen. The reaction mixture was then stirred at room temperature under nitrogen overnight. The resulting solution was poured into 200 mL of ice cooled NaHCO$_3$ aqueous and stirred for 30 minutes, the precipitate was collected by filtration, after dry obtained 12.2 g of clean product as an off white solid in 90% yield. $^1$H NMR (400 MHz, DMSO-d$_6$) δ 1.47 (s, 6H), 4.32 (s, 2H), 6.93 (d, J=8.8 Hz, 1H), 7.12 (d, J=8.0 Hz, 1H), 7.23 (s, 2H), 7.53 (t, J=8.8 Hz, 1H), 7.67 (d, J=6 Hz, 2H), 8.29 (s, 1H), 8.66 (d, J=6.4 Hz, 2H), 9.45 (s, 1H). MS 390 (MH$^+$).

Example 2

N-(1-((4-amino-2,2-dioxide-1H-benzo[c][1,2,6]thiadiazin-5-yl)oxy)-2-methylpropan-2-yl)-2-methylisonicotinamide

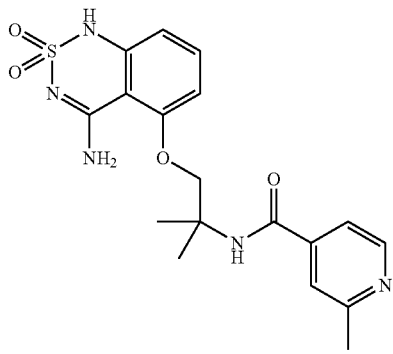 [SMILES: Cc1cc(C(=O)NC(C)(C)COc2cccc3c2C(N)=NS(=O)(=O)N3)ccn1]

To a stirred suspension of 5-(2-amino-2-methylpropoxy)-1H-benzo[c][1,2,6]thiadiazin-4-amine-2,2-dioxide hydrochloride (320.8 mg, 1 mmol) in DMF (8 mL) was added triethylamine (0.278 mL, 2 mmol). After being stirred at room temperature for 10 min., a mixture of 2-methylisonicotinic acid (151 mg, 1.1 mmol), EDCI (211 mg, 1.1 mmol) and HOBt (149 mg, 1.1 mmol) in 4 ml of DMF was added and the reaction mixture was then stirred at room temperature overnight. The resulting solution was purified by HPLC, and then the product was re-crystallized from ethanol/water, after dry to give the title compound as an off white solid (323 mg) in 80% yield. M.p.: 238-240° C. $^1$H NMR (400 MHz, DMSO-d$_6$) δ 1.48 (s, 6H), 2.52 (s, 3H), 4.39 (s, 2H), 6.63 (d, J=8.0 Hz, 1H), 6.79 (d, J=8.0 Hz, 1H), 7.45-7.49 (m, 2H), 7.52 (s, 1H), 7.83 (s, 1H), 8.43 (s, 1H), 8.50 (s, 1H), 8.54 (s, 1H), 11.00 (s, 1H). MS 404 (MH$^+$).

Example 3

N-(1-((4-amino-2,2-dioxide-1H-benzo[c][1,2,6]thiadiazin-5-yl)oxy)-2-methylpropan-2-yl)-2,6-dimethylisonicotinamide

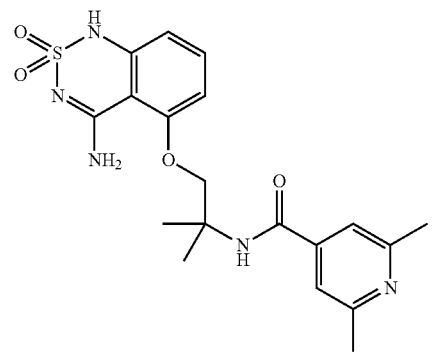 [SMILES: Cc1cc(C(=O)NC(C)(C)COc2cccc3c2C(N)=NS(=O)(=O)N3)cc(C)n1]

To a stirred suspension of 5-(2-amino-2-methylpropoxy)-1H-benzo[c][1,2,6]thiadiazin-4-amine-2,2-dioxide hydrochloride (320.8 mg, 1 mmol) in DMF (8 mL) was added triethylamine (0.278 mL, 2 mmol). After being stirred at room temperature for 10 min., a mixture of 2,6-dimethylisonicotinic acid (182 mg, 1.2 mmol), EDCI (191.7 mg, 1 mmol) and HOBt (135 mg, 1 mmol) in 4 ml of DMF was added and the reaction mixture was then stirred at room temperature overnight. The resulting solution was purified by HPLC, and then the product was re-crystallized from ethanol/water, after dry to give the title compound as an off white solid (237 mg) in 57% yield. M.p.: 240-241° C. $^1$H NMR (400 MHz, DMSO-d$_6$) δ 1.45 (s, 6H), 2.45 (s, 6H), 4.37 (s, 2H), 6.61 (d, J=8.0 Hz, 1H), 6.77 (d, J=8.0 Hz, 1H), 7.28 (s, 2H), 7.46 (t, J=8.0 Hz, 1H), 7.81 (s, 1H), 8.35 (s, 1H), 8.50 (s, 1H), 10.99 (s, 1H). MS 418 (MH$^+$).

Example 4

N4-(1-((4-amino-2,2-dioxido-1H-benzo[c][1,2,6]thiadiazin-5-yl)oxy)-2-methylpropan-2-yl)pyridine-2,4-dicarboxamide

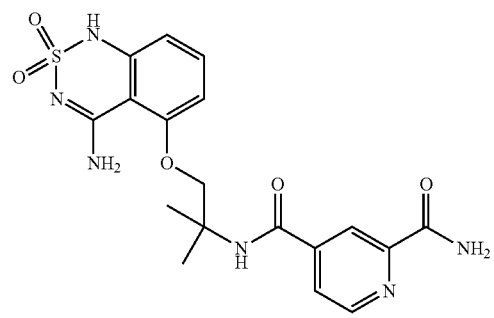 [SMILES: CC(C)(COc1cccc2c1C(N)=NS(=O)(=O)N2)NC(=O)c1ccnc(C(N)=O)c1]

To a solution of N-(1-((4-amino-2,2-dioxido-1H-benzo[c][1,2,6]thiadiazin-5-yl)oxy)-2-methylpropan-2-yl)-2-cyanoisonicotinamide (300 mg, 724 umol) in ethanol (20 mL) at room temperature, was added a solution of sodium hydroxide (275 mg, 7.06 mmol) in water (6 mL). The reaction was microwaved at 80° C. for five minutes, and upon completion was cooled 0° C., neutralized with 1N HCl, concentrated and purified by flash chromatography (1/9 methanol/dichloromethane). The purified product was washed with hot ethanol and the solid was collected by vacuum filtration and dried under vacuum at 50° C. to yield $N^4$-(1-((4-amino-2,2-dioxido-1H-benzo[c][1,2,6]thiadiazin-5-yl)oxy)-2-methylpropan-2-yl)pyridine-2,4-dicarboxamide (95 mg, 29%) as a white solid. $^1$H NMR (DMSO-$d_6$, 400 MHz): δ 1.50 (s, 6 H), 4.38 (s, 2H), 6.62 (d, J=0.8 Hz, 1H), 6.80 (d, J=8.4 Hz, 1 H), 7.47 (t, J=8.4 Hz, 1H), 7.75 (s, 1H), 7.80 (s, 1H), 7.86 (dd, J=5.2 Hz, 1H), 8.19 (s, 1H), 8.35 (s, 1H), 8.39 (s, 1H), 8.69 (s, 1H), 8.73 (dd, J=4.8 Hz, 1H), 10.99 (s, 1H). MS 433 (MH$^+$).

Example 5

N-(1-((4-amino-2,2-dioxido-1H-benzo[c][1,2,6]thiadiazin-5-yl)oxy)-2-methylpropan-2-yl)-2-(methylamino)isonicotinamide

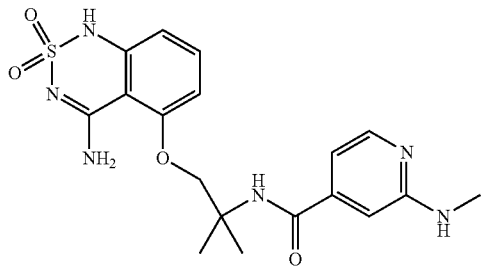 [SMILES: CNc1cc(C(=O)NC(C)(C)COc2cccc3c2C(N)=NS(=O)(=O)N3)ccn1]

To a solution of 2-(methylamino)isonicotinic acid (120 mg, 0.780 mmol) in DMF (24 mL) were added EDCI (150 mg, 0.780 mmol), HOBt (105 mg, 0.780 mmol), and 5-(2-amino-2-methylpropoxy)-1H-benzol[c][1,2,6]thiadiazin-4-amino-2,2-dioxide hydrochloride (250 mg, 0.780) followed by triethylamine (220 uL, 1.56 mmol). The reaction was stirred at room temperature for 12 hours under nitrogen. Upon completion, the reaction was diluted with water and extracted with ethyl acetate (3×). The organic extracts were combined, dried over Na$_2$SO$_4$, filtered, and concentrated. The residue was purified by HPLC (10-90% acetonitrile in water) and the clean fractions were combined and concentrated. The solid was suspended in water (2 mL) and solid NaHCO$_3$ (80 mg) was added and the suspension was stirred at 80° C. for 20 minutes. The clear solution was cooled to 0° C. and neutralized with 1N HCl. The precipitate was collected by vacuum filtration and dried under high vacuum to afford N-(1-((4-amino-2,2-dioxido-1H-benzo[c][1,2,6]thiadiazin-5-yl)oxy)-2-methylpropan-2-yl)-2-(methylamino)isonicotinamide (180 mg, 56% yield). $^1$H NMR (400 MHz, DMSO-$d_6$) δ 1.45 (s, 6H), 2.78 (d, J=4.8 Hz, 3H), 4.34 (s, 2H), 6.58-6.65 (m, 3H), 6.72 (d, J=1.2 Hz, 1H), 6.73 (d, J=1.2 Hz, 1H), 7.42 (t, J=8.0 Hz, 1H), 7.80 (br s, 1H), 8.03 (d, J=5.2 Hz, 1H), 8.23 (s, 1H), 8.30 (br s, 1H), 10.98 (br s, 1H) MS 419 (MH$^+$).

Example 6

N-(1-((4-amino-2,2-dioxido-1H-benzo[c][1,2,6]thiadiazin-5-yl)oxy)-2-methylpropan-2-yl)-2-(1H-imidazol-1-yl)isonicotinamide

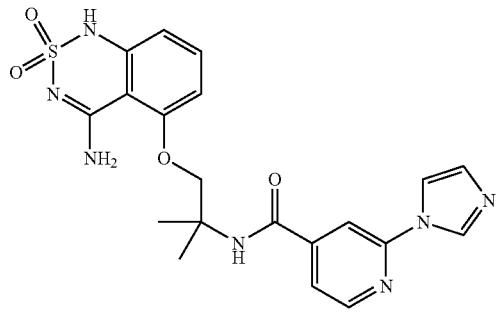 [SMILES: CC(C)(COc1cccc2c1C(N)=NS(=O)(=O)N2)NC(=O)c1ccnc(-n2ccnc2)c1]

To a solution of 2-(1H-imidazol-1-yl)isonicotinic acid (1.00 g, 5.29 mmol), in DMF (41 mL) at room temperature, was added HOBt.H$_2$O (891 mg, 5.82 mmol), EDCI.HCl (1.11 g, 5.82 mmol), 4-amino-5-(2-amino-2-methylpropoxy)-1H-benzo[c][1,2,6]thiadiazine 2,2-dioxide hydrochloride (1.70 g, 5.29 mmol) and triethylamine (1.54 mL, 11.1 mmol). The reaction was heated to 50° C. for one hour, and upon completion was cooled to room temperature, filtered and the filtrate was purified by HPLC (10-90% acetonitrile in water), then the purified product was washed in boiling ethanol for thirty minutes, then cooled to room temperature. The solid was collected by vacuum filtration, sodium carbonate (178 mg) in water (50 mL) was added and the mixture was heated to 60° C. until in solution, then was cooled to 0° C. and neutralized with hydrochloric acid (1N). The white solid was collected by vacuum filtration and dried under vacuum at 50° C. (295 mg). Sodium carbonate (87.3 mg) in water (7 mL) was added to the white solid and the mixture was heated to 60° C. until in solution. The warm solution was filtered, cooled to room temperature, and neutralized with hydrochloric acid (1N). The white solid was collected by vacuum filtration and dried under vacuum at 50° C. to yield N-(1-((4-amino-2,2-dioxido-1H-benzo[c][1,2,6]thiadiazin-5-yl)oxy)-2-methylpropan-2-yl)-2-(1H-imidazol-1-yl)isonicotinamide as a white solid (171 mg, 7% yield). $^1$H NMR (DMSO-$d_6$, 400 MHz): δ 1.50 (s, 6 H), 4.41 (s, 2H), 6.62 (d, J=8.0 Hz, 1H), 6.79 (d, J=8.0 Hz, 1 H), 7.14 (s, 1H), 7.47 (t, J=8.4 Hz, 1H), 7.63 (dd, J=6.0 Hz, 1H), 7.81 (s, 1H), 8.00 (d, J=8.0 Hz, 1H), 8.47 (s, 1H), 8.58 (m, 3H), 11.00 (s, 1H). MS 456 (MH$^+$).

Example 7

N-(1-((4-amino-2,2-dioxido-1H-benzo[c][1,2,6]thiadiazin-5-yl)oxy)-2-methylpropan-2-yl)-2-(1H-1,2,4-triazol-1-yl)isonicotinamide

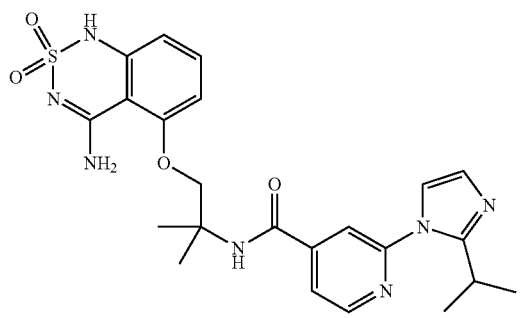 [SMILES: CC(C)c1nccn1-c1cc(C(=O)NC(C)(C)COc2cccc3c2C(N)=NS(=O)(=O)N3)ccn1]

To a solution of 2-(2-isopropyl-1H-imidazol-1-yl)isonicotinic acid (432 mg, 1.87 mmol, Example 7a) in DMF (29 mL) at room temperature, was added HOBt.H$_2$O (286 mg, 1.87 mmol), EDCI.HCl (358 mg, 1.87 mmol), 4-amino-5-(2-amino-2-methylpropoxy)-1H-benzo[c][1,2,6]thiadiazine 2,2-dioxide hydrochloride (600 mg, 1.87 mmol, Example 1a) and triethylamine (518 uL, 3.74 mmol). The reaction was heated to 50° C. for two hour, and upon completion was cooled to room temperature, and the residue was purified by HPLC (10-90% acetonitrile in water), then repurified by flash chromatography (1/9 MeOH/CH$_2$Cl$_2$). The purified product (303 mg, 33% yield) was suspended in water (10 mL) and sodium carbonate was added (96.8 mg, 913 umol). The mixture was heated to 45° C. until in solution. The solution was cooled to room temperature and neutralized with hydrochloric acid (1N). The precipitate was collected by vacuum filtration and dried under vacuum at 50° C. to yield N-(1-((4-amino-2,2-dioxido-1H-benzo[c][1,2,6]thiadiazin-5-yl)oxy)-2-methylpropan-2-yl)-2-(1H-1,2,4-triazol-1-yl) isonicotinamide (210 mg, 23%) as a white solid. $^1$H NMR (DMSO-d$_6$, 400 MHz): δ 1.15 (d, J=6.4 Hz, 6H), 1.49 (s, 6H), 3.46 (m, J=6.4 Hz, 1H), 4.38 (s, 2H), 6.61 (d, J=8.4 Hz, 1H), 6.79 (d, J=8.0 Hz, 1H), 6.94 (s, 1H), 7.46 (t, J=8.4 Hz, 1H), 7.52 (s, 1H), 7.74 (dd, J=3.6 Hz, 1H), 7.81 (s, 2H), 8.66 (dd, J=4.8 Hz, 1H), 11.00. MS 498 (MH$^+$).

Example 7a 2-(2-isopropyl-1H-imidazol-1-yl)isonicotinic acid

A mixture of methyl 2-bromoisonicotinate (2.00 g, 9.26 mmol), 2-isopropyl-1H-imidazole (1.12 g, 10.2 mmol), cesium carbonate (6.03 g, 18.5 mmol) and copper(1) Iodide (176 mg, 926 umol) in DMSO was heated to 120° C. for eighteen hours, under nitrogen. The crude material was filtered, purified by preparative HPLC (10-90% CH$_3$CN in water). The pure fractions were collected and concentrated to give 2-(2-isopropyl-1H-imidazol-1-yl)isonicotinic acid as a white sticky solid (1.176 g, 55% yield). MS 232 (MH$^+$).

Example 8

Synthesis of N-(1-((4-amino-2,2-dioxido-1H-benzo[c][1,2,6]thiadiazin-5-yl)oxy)-2-methylpropan-2-yl)-2-(1H-1,2,4-triazol-1-yl)isonicotinamide

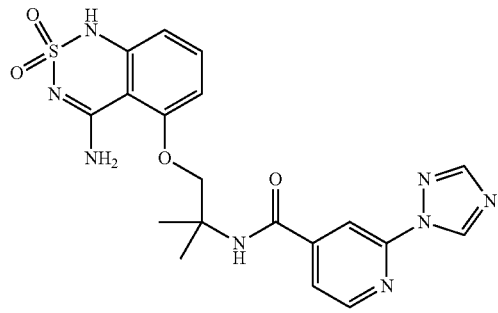 [SMILES: CC(C)(COc1cccc2c1C(N)=NS(=O)(=O)N2)NC(=O)c1ccnc(-n2cncn2)c1]

A mixture of N-(1-((4-amino-2,2-dioxido-1H-benzo[c][1,2,6]thiadiazin-5-yl)oxy)-2-methylpropan-2-yl)-2-bromoisonicotinamide (750 mg, 1.60 mmol), 1H-1,2,4-triazole (122 mg, 1.76 mmol), cesium carbonate (782 mg, 2.40 mmol) and copper(1) Iodide (76.2 mg, 0.400 mmol) in DMF was heated to 120° C. for eighteen hours, under nitrogen. The crude material was filtered, purified by preparative HPLC (10-90% CH$_3$CN in water), then purified by flash chromatography (7/93 methanol/dichloromethane). The pure fractions were collected, concentrated, transferred to a small vial using ethanol to partially dissolve. The mixture was concentrated, and a suspension was formed in water (3 mL) and sodium carbonate was added (86.4 mg, 815 umol). The suspension was heated to 70° C. until fully dissolved. The solution was brought to room temperature and the pH was neutralized with hydrochloric acid (1N). The precipitate was collected by vacuum filtration and dried under vacuum at 60° C. to give N-(1-((4-amino-2,2-dioxido-1H-benzo[c][1,2,6]thiadiazin-5-yl)oxy)-2-methylpropan-2-yl)-2-bromoisonicotinamide as a white solid (155 mg, 21% yield). $^1$H NMR (DMSO-d$_6$, 400 MHz): δ 1.49 (s, 6H), 4.39 (s, 2H), 6.61 (d, J=7.6 Hz, 1H), 6.79 (d, J=8.0 Hz, 1 H), 7.46 (t, J=8.0 Hz, 1H), 7.76 (dd, J=4.4 Hz, 1H), 7.78 (s, 1H), 8.15 (s, 1H), 8.33 (s, 1H), 8.37 (s, 1H), 8.63 (dd, J=6.0 Hz, 1H), 8.71 (s, 1H), 9.40 (s, 1H), 10.98 (s, 1H). MS 457 (MH$^+$).

Example 9

N-(1-(((4-amino-2,2-dioxido-1H-benzo[c][1,2,6]thiadiazin-5-yl)oxy)methyl)cyclopentyl)isonicotinamide

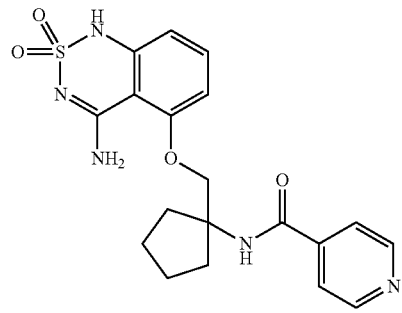 [SMILES: NC1=NS(=O)(=O)Nc2cccc(OCC3(NC(=O)c4ccncc4)CCCC3)c21]

To a stirred suspension of 4-amino-5-((1-aminocyclopentyl)methoxy)-1H-benzo[c][1,2,6]thiadiazine 2,2-dioxide hydrochloride (346.83 mg, 1 mmol) in DMF (6 mL) was added triethylamine (0.278 mL, 2 mmol). After being stirred at room temperature for 10 min., a mixture of isonicotinic acid (123.11 mg, 1.1 mmol), EDCI (211 mg, 1.1 mmol) and HOBt (149 mg, 1.1 mmol) in 4 ml of DMF was added and the reaction mixture was then stirred at room temperature overnight. The resulting solution was purified by reverse phase HPLC, and then the product was re-crystallized from ethanol/water, after dry to give the title compound as a white solid (300 mg) in 72% yield. M.p.: >250° C. $^1$H NMR (400 MHz, DMSO-d$_6$) δ 1.65-1.67 (m, 2H), 1.75-1.78 (m, 2H), 1.83-1.88 (m, 2H), 2.19-2.24 (m, 2H), 4.43 (s, 2H), 6.59 (d, J=8.0 Hz, 1H), 6.79 (d, J=8.0 Hz, 1H), 7.43 (t, J=8.0 Hz, 1H), 7.66 (d, J=8.0 Hz, 2H), 7.85 (s, 1H), 8.43 (s, 1H), 8.56 (s, 1H), 8.66 (d, J=8 Hz, 2H), 10.96 (s, 1H). MS 416 (MH$^+$).

Example 10

Synthesis of N-(1-(((4-amino-2,2-dioxido-1H-benzo[c][1,2,6]thiadiazin-5-yl)oxy)methyl)cyclopentyl)-2-methylisonicotinamide

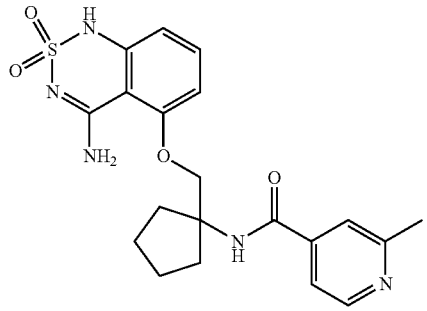 [SMILES: Cc1cc(C(=O)NC2(COc3cccc4c3C(N)=NS(=O)(=O)N4)CCCC2)ccn1]

To a solution of 4-amino-5-(1-aminocyclopentyl)methoxy)-1H-benzo[c][1,2,6]thiadiazine-2,2-dioxide hydrochloride (252 mg, 0.72 mmol) in DMF (7 mL) was added triethylamine (202 uL, 1.45 mmol), followed by a solution of 2-methylpyridine-4-carboxylic acid (99 mg, 0.72 mmol), EDCI HCl (138 mg, 0.72 mmol), and HOBt hydrate (110 mg, 0.72 mmol) in DMF (5 mL). The reaction was stirred at room temperature for 24 h, and the resulting solution was purified by HPLC (10-90% acetonitrile in water). After removal of the solvent, the residue was suspended in an aqueous solution of NaHCO$_3$ (208 mg in 3 mL of water) and heated to 95° C. After complete dissolution, the mixture was cooled to 0° C., neutralized with 1N HCl, and the resulting precipitate was collected by vacuum filtration to provide N-(1-(((4-amino-2,2-dioxido-1H-benzo[c][1,2,6]thiadiazin-5-yl)oxy)methyl)cyclopentyl)-2-methylisonicotinamide (124.1 mg, 40%) as a white solid. $^1$H NMR (400 MHz, DMSO-d$_6$) δ 1.66 (m, 2H), 1.74 (m, 2H), 1.82 (m, 2H), 2.19 (m, 2H), 2.50 (s, 3H), 4.42 (s, 2H), 6.59 (d, J=8.4 Hz, 1H), 6.77 (d, J=8.4 Hz, 1H), 7.42 (t, J=8.4 Hz, 1H), 7.44 (m, 1H), 7.51 (s, 1H), 7.83 (br s, 1H), 8.40 (br s, 1H), 8.49 (s, 1H), 8.51 (d, J=5.1 Hz, 1H), 10.95 (br s, 1H). MS 430 (MH$^+$).

Example 11

N-(1-(((4-amino-2,2-dioxido-1H-benzo[c][1,2,6]thiadiazin-5-yl)oxy)methyl)cyclopentyl)-2-(methylamino)isonicotinamide

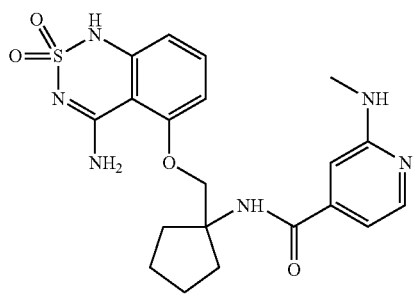 [SMILES: CNc1cc(C(=O)NC2(COc3cccc4c3C(N)=NS(=O)(=O)N4)CCCC2)ccn1]

To a stirred suspension of 4-amino-5-((1-aminocyclopentyl)methoxy)-1H-benzo[c][1,2,6]thiadiazine 2,2-dioxide hydrochloride (200 mg, 0.577 mmol) in DMF (5 mL) was added triethylamine (0.32 mL, 2.31 mmol). After being stirred at room temperature for 10 min., a mixture of 2-(methylamino)isonicotinic acid (88 mg, 0.577 mmol), EDCI (122 mg, 0.635 mmol) and HOBt (86 mg, 0.635 mmol) in 10 ml of DMF were added, and the reaction mixture was then stirred at room temperature overnight and at 55° C. for 2 hrs. The resulting solution was purified by preparative HPLC (10-90% CH$_3$CN in water). The clean fractions were collected and re-crystallized from ethanol/water, dried at 60° C. under vacuum to provide the title compound (87 mg) in 34% yield. $^1$H NMR (400 MHz, DMSO-d$_6$) δ 1.62-1.84 (m, 6H), 2.15-2.21 (m, 2H), 2.76 (J=4.8 Hz, 3H), 4.40 (s, 2H), 6.59-6.64 (m, 3H), 6.70-6.72 (m, 1H), 6.77 (d, J=8.0 Hz, 1H), 7.43 (t, J=8.8 Hz, 1H), 7.88 (s, 1H), 8.00 (d, J=5.2 Hz, 1H), 8.33 (s, 1H), 8.38 (s, 1H), 10.97 (s, 1H). MS 445 (MH$^+$).

The compounds below were synthesized following the procedures similar to those described in the above Examples.

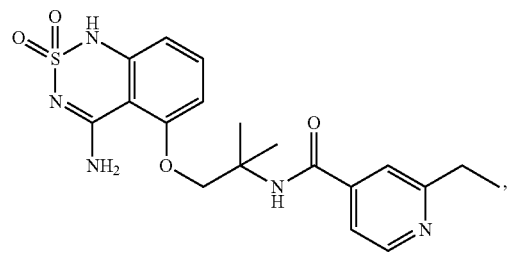

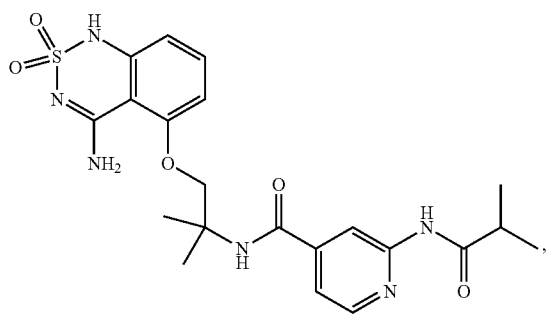

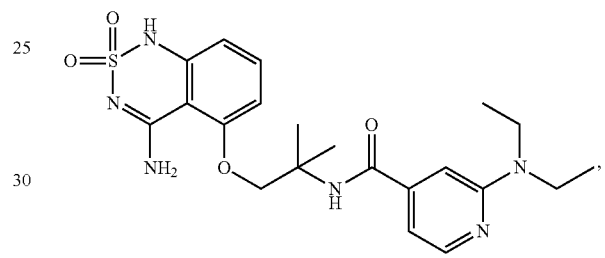

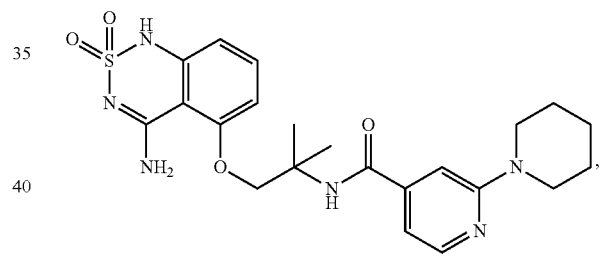

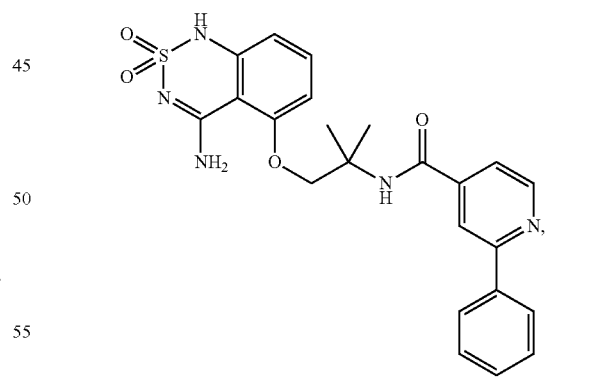

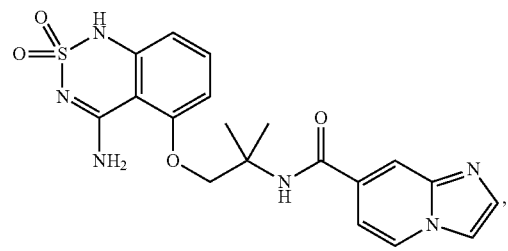

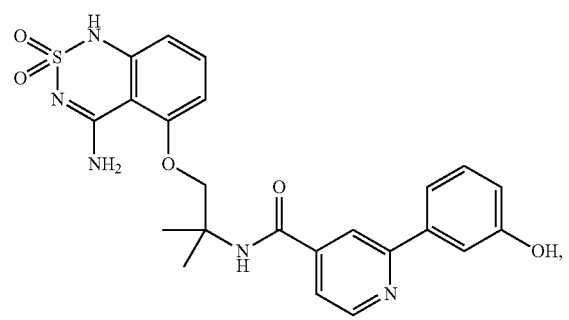
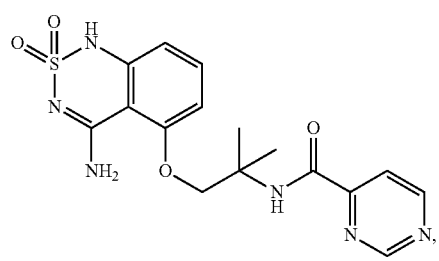
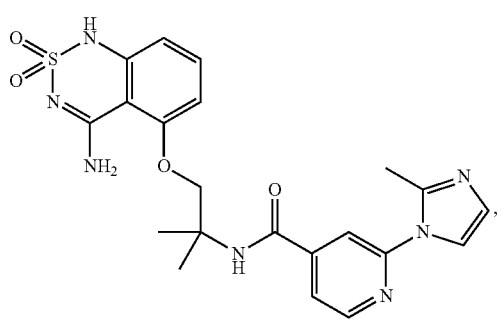
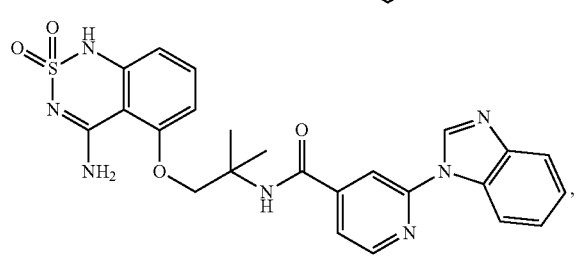
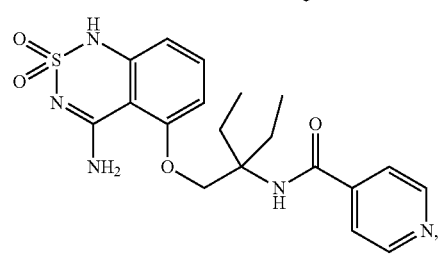
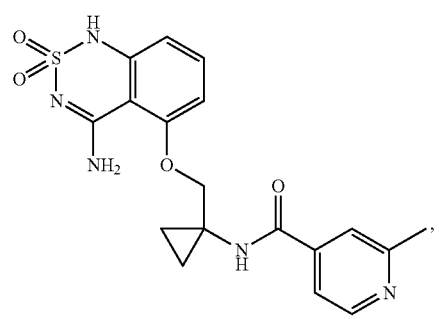
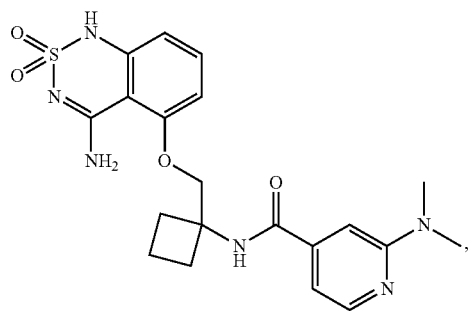
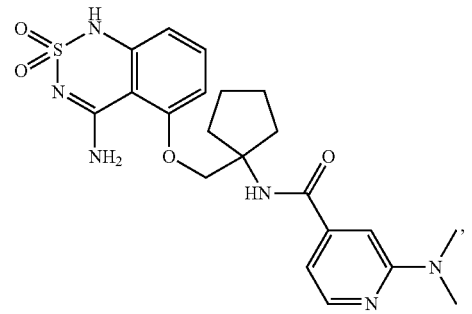
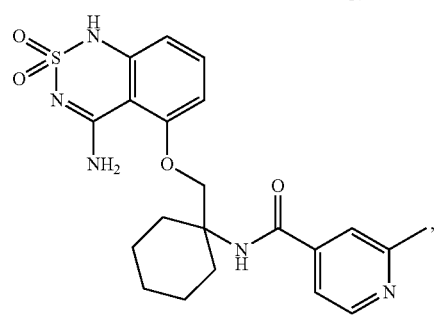
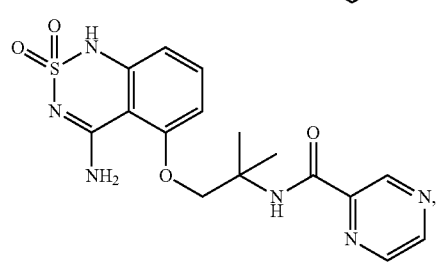
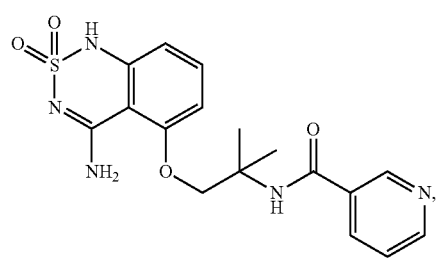
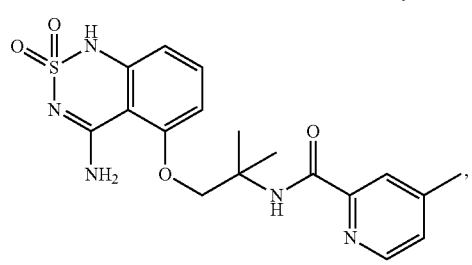

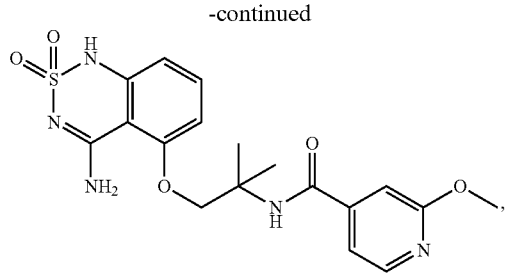

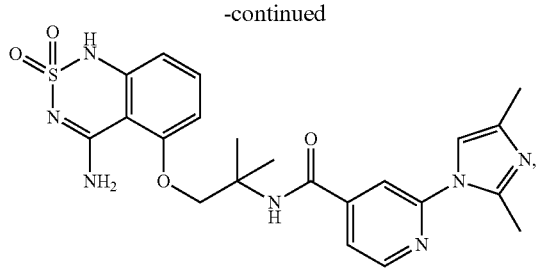

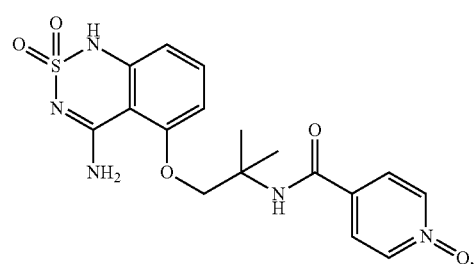

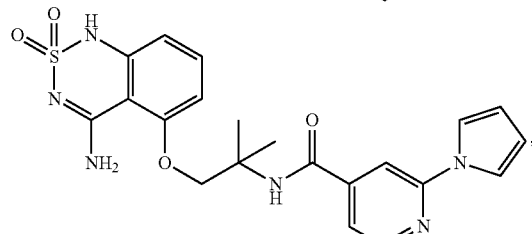

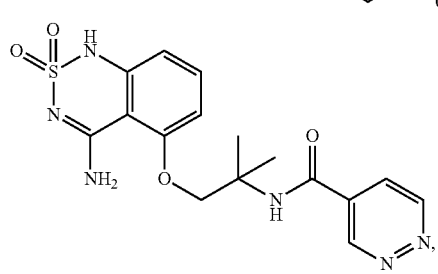

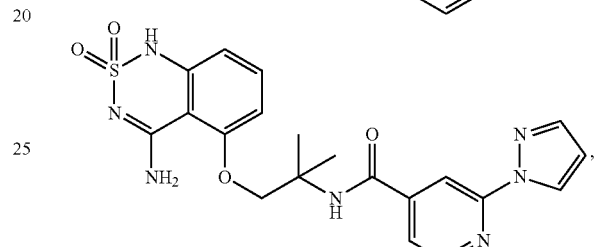

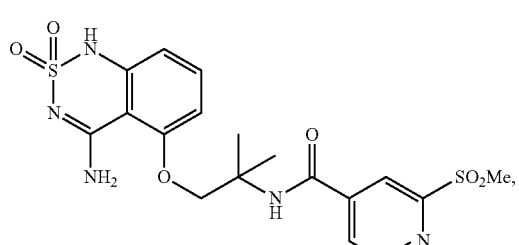

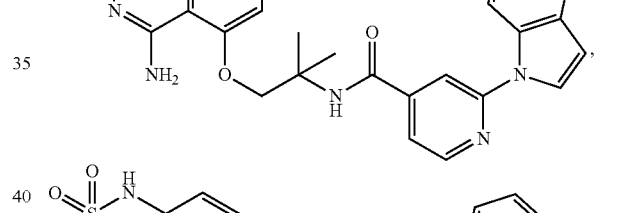

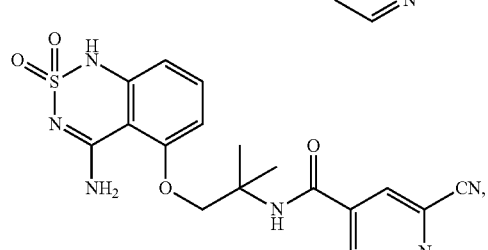

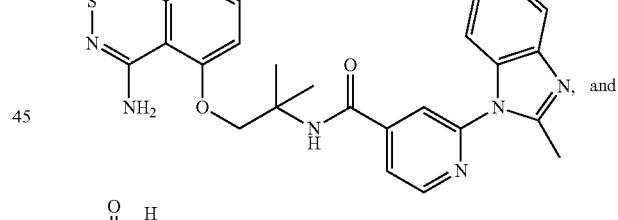

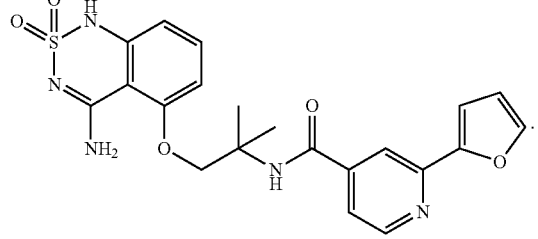

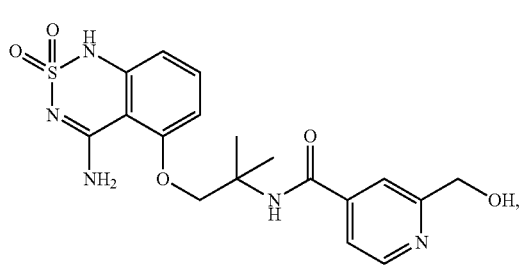

Biological Tests

The present compounds have been tested and shown sweet taste enhancing activities. Specifically, the present compounds have demonstrated activation of the T1R2/T1R3 receptor and potentiation or enhancement of the activation of the T1R2/T1R3 receptor as well as sweet taste enhancing activities for sweetener, such as sucrose and fructose. Compounds A1 to A9, B1, and B2 in Experiment 1 below for the human taste tests are selected compounds described above. For example, Compound A1 is Example 1.

Experiment 1

Sweet Flavor and Sweet Flavor Enhancement Measurement Using Human Panelists Conducting a Paired Comparison Test Test samples containing experimental compounds are presented in pairs to the panelist and they are asked to determine which of the sample is sweeter. The present compounds showed sweet flavor enhancement in medium with a wide range of pH value, and this Experiment provided results for samples tested at pH of about 7.1 or about 2.8. A group of 10 to 16 or more panelists participated in each test. Subjects refrained from eating or drinking (except water) for at least 1 hour prior to the test. Subjects rinsed with water several times to clean the mouth.

Taste tests were performed with sucrose or HFCS as the sweetener in the presence or absence of compound. A 0.2% stock solution of compound in water with sodium bicarbonate was prepared and then this stock solution was diluted in the final sample to achieve the targeted final concentration of compound. Taste samples were also prepared in a low sodium phosphate buffer (pH 7.1; "LSB") lacking sucrose or HFCS to evaluate the taste of the compound alone. Low sodium phosphate buffer consists of 0.3 mM KCl, 0.5 mM $Na_2HPO_4$, and 0.175 mM $KH_2PO_4$. Sample volumes are usually 20 ml.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05.

A. Sweetness Threshold: Paired comparison taste test for sweetness with LSB+compound at pH 7.1 vs. 1% Sucrose at pH 7.1

| Compound | Results |
|---|---|
| A1 | 25 ppm equivalent to 1% sucrose |
| A2 | 10 ppm less sweet than 1% sucrose |
| A3 | 10 ppm less sweet than 1% sucrose |
| A4 | 10 ppm less sweet than 1% sucrose |
| A5 | 10 ppm less sweet than 1% sucrose |
| A6 | 10 ppm equivalent to 1% sucrose |
| A7 | 10 ppm less sweet than 1% sucrose |
| A8 | 10 ppm less sweet than 1% sucrose |
| A9 | 15 ppm equivalent to 1% sucrose |
| B1 | 25 ppm equivalent to 1% sucrose |
| B2 | 5 ppm less sweet than 1% sucrose |

B. Enhancement of Sucrose at pH 7.1: Paired comparison taste test with 6% sucrose+compound at pH 7.1 vs. 10%, 11% or 12% Sucrose at pH 7.1

| Compound | Results |
|---|---|
| A1 | 10 ppm in 6% sucrose is equivalent to 10% sucrose |
| A2 | 5 ppm in 6% sucrose is equivalent to 10% sucrose |
| A3 | 5 ppm in 6% sucrose is equivalent to 10% sucrose |
| A4 | 5 ppm in 6% sucrose is equivalent to 10% sucrose |
| A5 | 5 ppm in 6% sucrose is equivalent to 10% sucrose |
| A6 | 5 ppm in 6% sucrose is equivalent to 11% sucrose |
| A7 | 5 ppm in 6% sucrose is equivalent to 10% sucrose |
| A8 | 5 ppm in 6% sucrose is equivalent to 10% sucrose |
| A9 | 15 ppm in 6% sucrose is equivalent to 12% sucrose |
| | 10 ppm in 6% sucrose is equivalent to 10% sucrose |
| B1 | 5 ppm in 6% sucrose is equivalent to 10% sucrose |
| B2 | 5 ppm in 6% sucrose is equivalent to 10% sucrose |

C. Enhancement of Sucrose at pH 2.8: Paired comparison taste test with 6% sucrose+compound at pH 2.8 vs. 10%, 11% or 12% Sucrose at pH 2.8

| Compound | Results |
|---|---|
| A1 | 10 ppm in 6% sucrose is equivalent to 12% sucrose |
| | 5 ppm in 6% sucrose is equivalent to 11% sucrose |
| A2 | 5 ppm in 6% sucrose is equivalent to 12% sucrose |
| A5 | 5 ppm in 6% sucrose is equivalent to 12% sucrose |
| A6 | 5 ppm in 6% sucrose is equivalent to 12% sucrose |
| A7 | 5 ppm in 6% sucrose is equivalent to 12% sucrose |
| A9 | 7 ppm in 6% sucrose is equivalent to 12% sucrose |
| | 5 ppm + 6% in 6% sucrose is equivalent to 10% sucrose |
| B2 | 5 ppm in 6% sucrose is equivalent to 12% sucrose |

D. Enhancement of HFCS at pH 2.8: Paired comparison taste test with 6% HFCS+compound at pH 2.8 vs. 8% or 9% HFCS at pH 2.8

| Compound | Results |
|---|---|
| A1 | 20 ppm in 6% HFCS is equivalent to 9% HFCS |
| A2 | 10 ppm in 6% HFCS is equivalent to 8% HFCS |
| A3 | 10 ppm in 6% HFCS is equivalent to 8% HFCS |
| A5 | 10 ppm in 6% HFCS is equivalent to 8% HFCS |
| A6 | 10 ppm in 6% HFCS is equivalent to 9% HFCS |
| | 8 ppm in 6% HFCS is equivalent to 8% HFCS |
| A7 | 10 ppm in 6% HFCS is equivalent to 8% HFCS |
| A8 | 10 ppm in 6% HFCS is equivalent to 8% HFCS |
| A9 | 15 ppm in 6% HFCS is equivalent to 8% HFCS |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound having structural Formula (I):

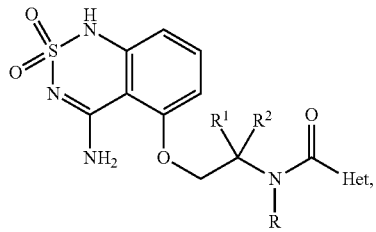

or a salt or solvate thereof; wherein $R^1$ and $R^2$ are independently C1 to C4 alkyl; or alternatively, $R^1$ and $R^2$, together with the carbon atom to which they are attached, form a C3 to C7 cycloalkyl;

R is hydrogen or C1 to C6 alkyl; and

Het is heteroaryl or substituted heteroaryl, wherein the substituents are selected from the group consisting of —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

2. The compound of claim 1, wherein R is hydrogen.

3. The compound of claim 1, wherein $R^1$ and $R^2$ are both methyl, ethyl, or propyl.

4. The compound of claim 1, wherein $R^1$ and $R^2$, together with the carbon atom to which they are attached, form cyclopropyl, cyclobutyl, cylclopentyl, or cyclohexyl.

5. The compound of claim 2, wherein Het is an optionally substituted monocyclic five or six-membered heteroaryl containing one or more heteroatoms selected from the group of N, O, and S.

6. The compound of claim 5, wherein Het is an optionally substituted pyridine, pyrimidine, N-oxide pyridine, or N-oxide pyrimidine.

7. The compound of claim 2, wherein Het is an optionally substituted bicyclic ten to twelve-membered heteroaryl containing one or more heteroatoms selected from the group of N, O, and S.

8. The compound of claim 1, which is represented by structural Formula (Ia):

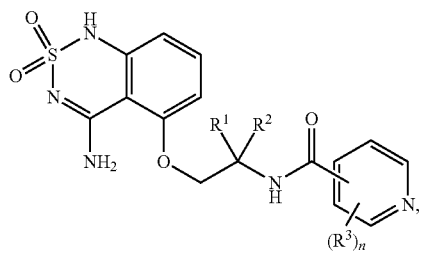

wherein, n is 0, 1, 2, or 3; and $R^3$ is halo, cyano, hydroxyl, amine, alkoxy, alkylamine, acyl, acylamine, amide, sulfonamide, ester, alkyl, substituted alkyl, heteroalkyl, substituted heteroalkyl, aryl, substituted aryl, heteroaryl, substituted heteroaryl, carbocyclyl, or substituted carbocyclyl.

9. The compound of claim 8, wherein $R^1$ and $R^2$ are both methyl, ethyl, or propyl.

10. The compound of claim 8, wherein $R^1$ and $R^2$, together with the carbon atom to which they are attached, form cyclopropyl, cyclobutyl, cylclopentyl, or cyclohexyl.

11. The compound of claim 8, which is represented by structural Formula (Ib):

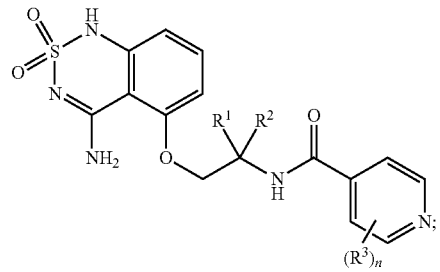

$R^1$ and $R^2$ are independently C1 to C4 alkyl; or alternatively, $R^1$ and $R^2$, together with the carbon atom to which they are attached, form a C3 to C7 cycloalkyl;

n is 0, 1, 2, or 3; and $R^3$ is halo, cyano, hydroxyl, amine, alkoxy, alkylamine, acyl, acylamine, amide, sulfonamide, ester, alkyl, substituted alkyl, heteroalkyl, substituted heteroalkyl, aryl, substituted aryl, heteroaryl, substituted heteroaryl, carbocyclyl, or substituted carbocyclyl.

12. The compound of claim 1, which is selected from the group consisting of

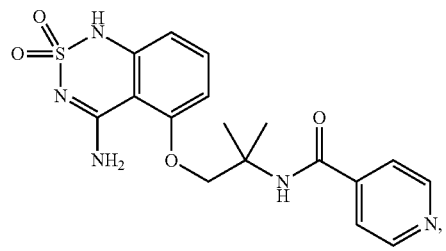

49
-continued
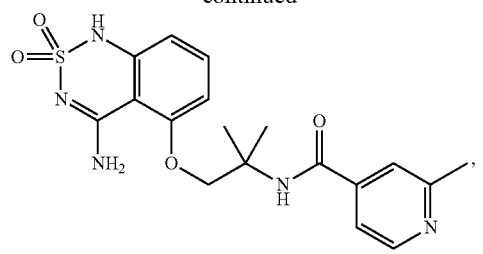
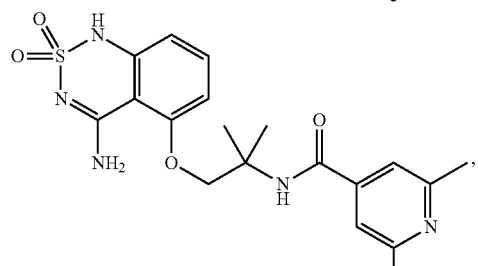
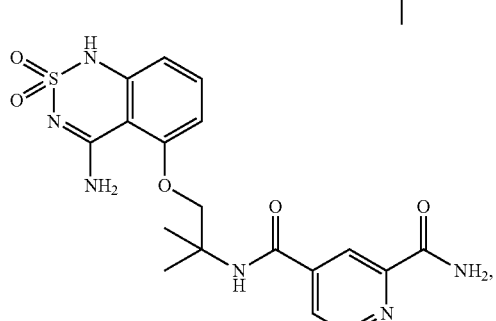
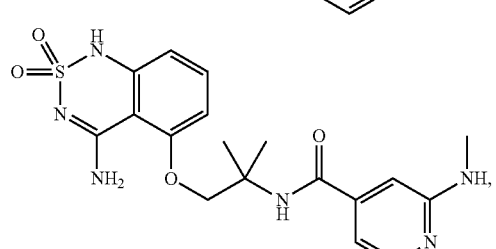
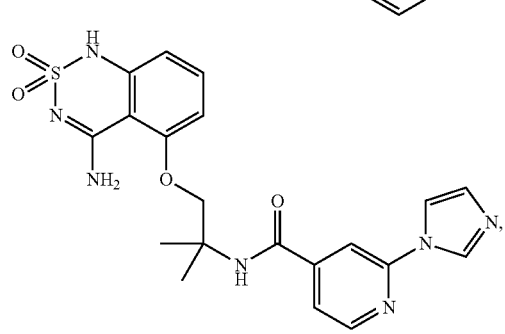
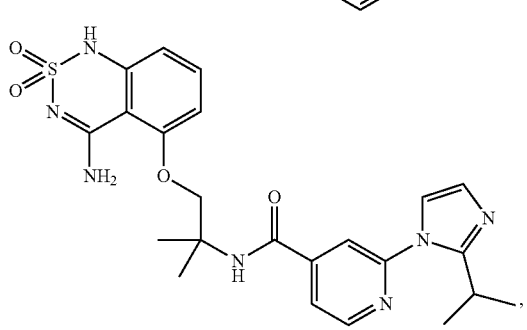
50
-continued
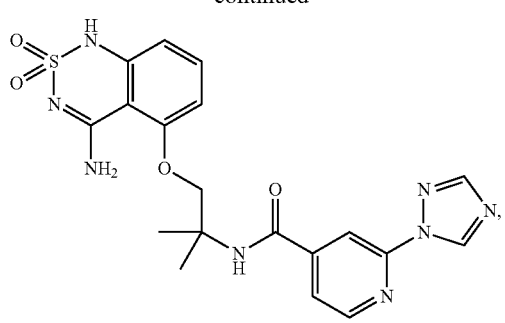
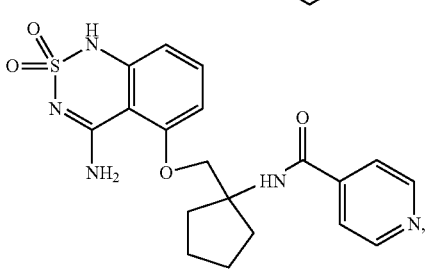
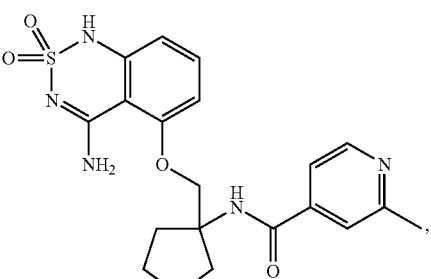
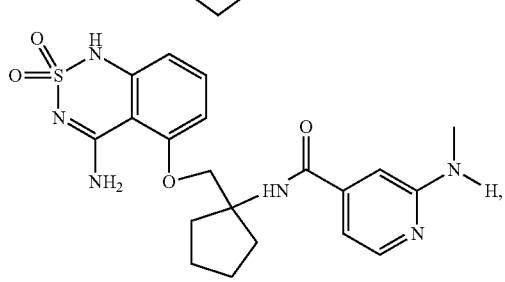
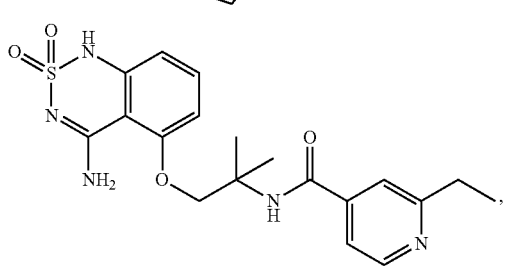
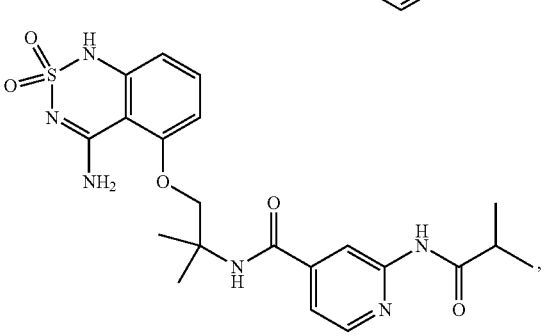

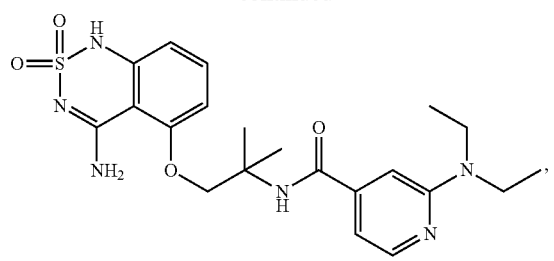
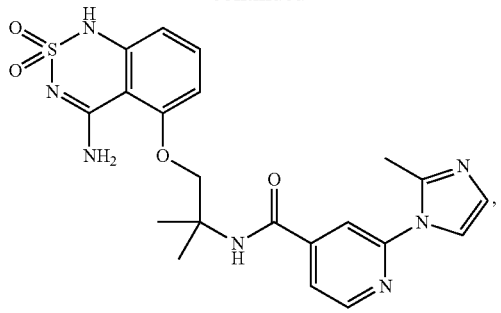
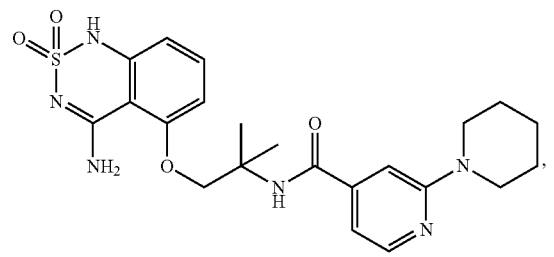
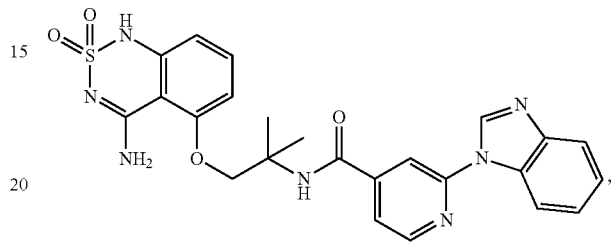
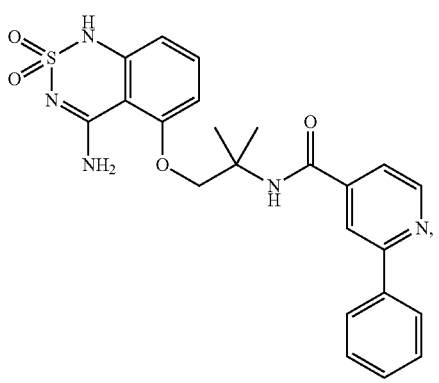
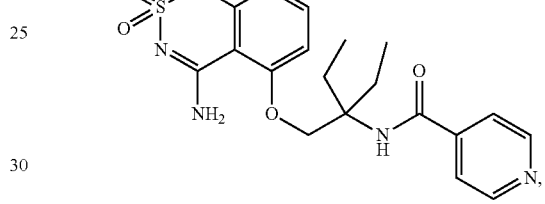
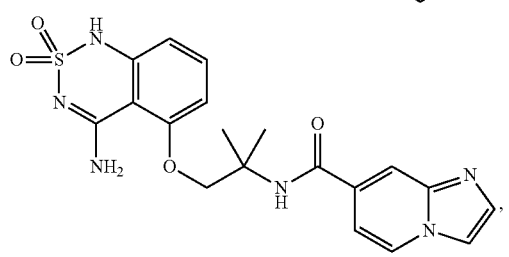
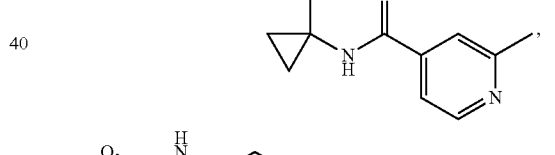
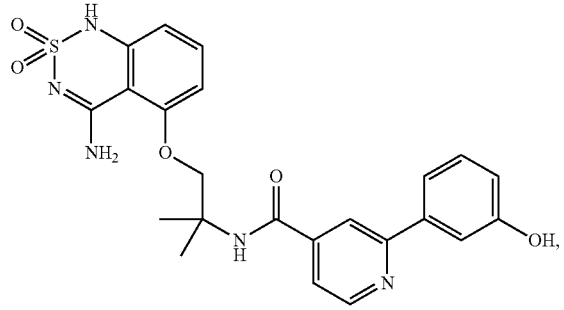
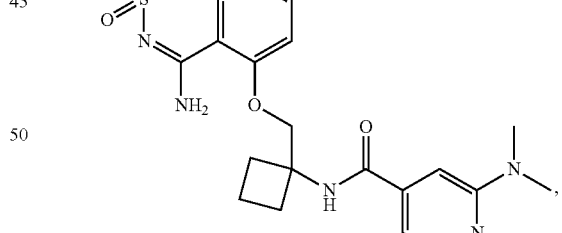
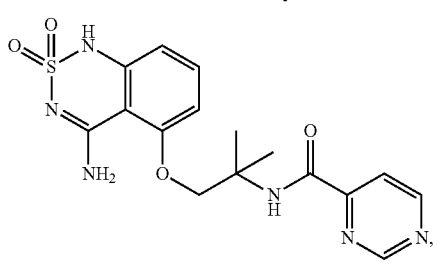

53
-continued
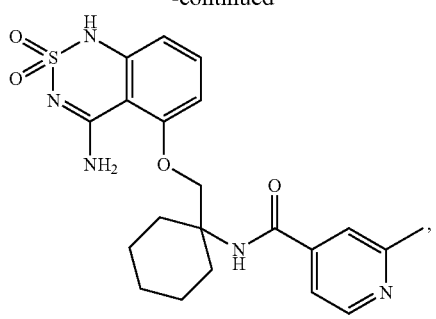
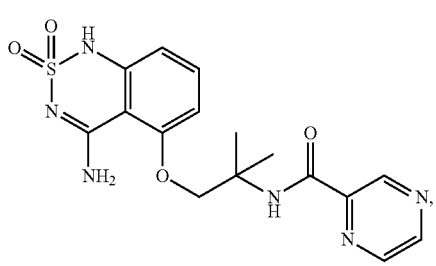
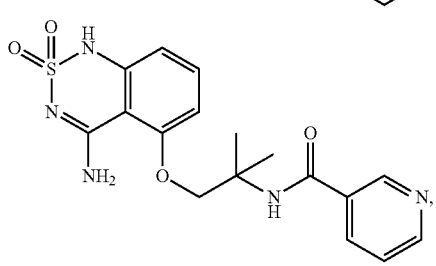
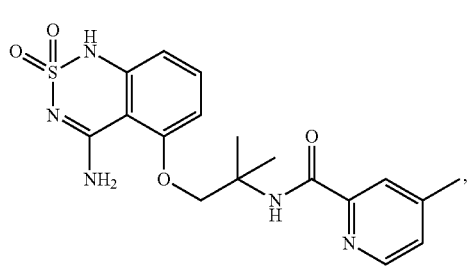
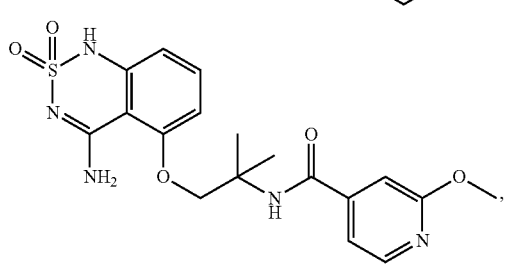
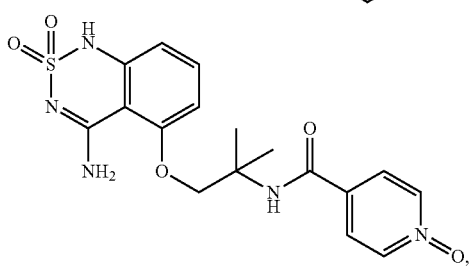
54
-continued
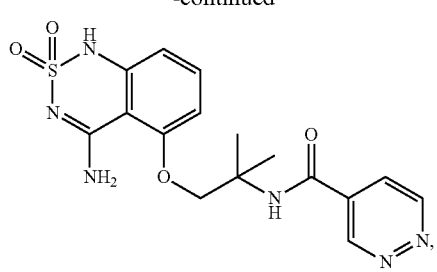
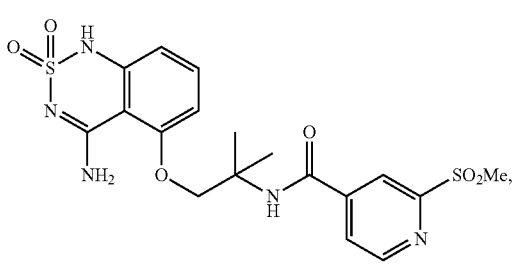
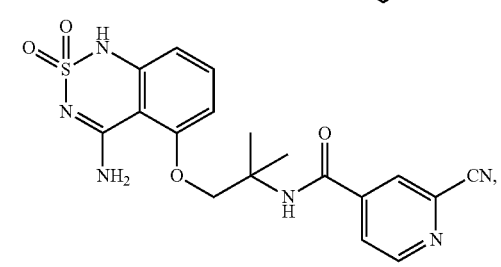
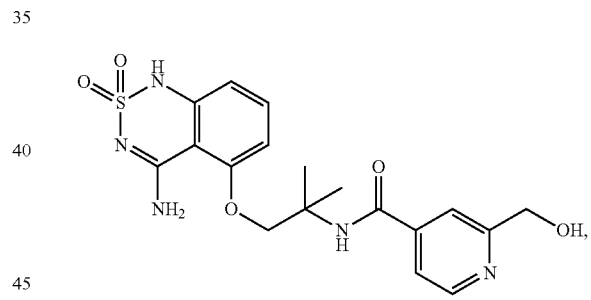
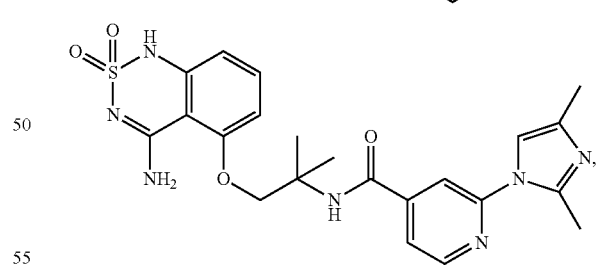
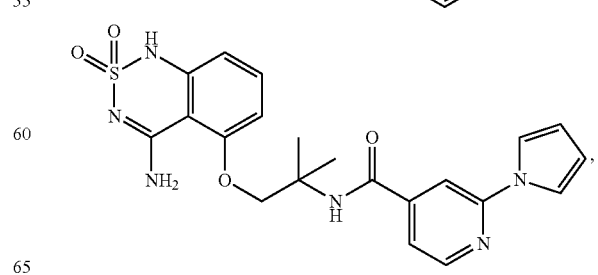

-continued

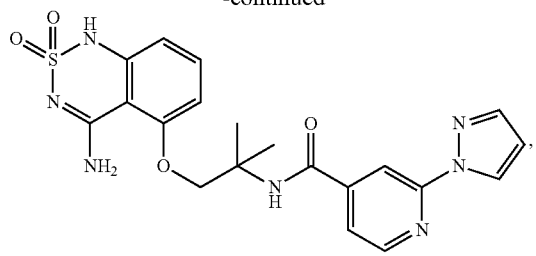

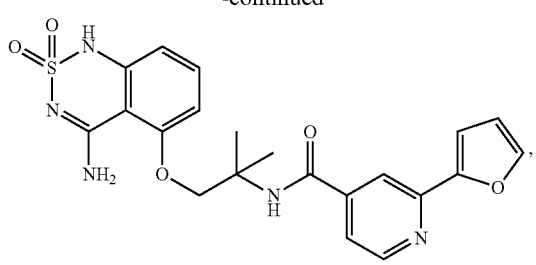

or a salt or solvate thereof.

13. The compound of claim 1, wherein the substituents are selected from the group consisting of —$R^a$, halo, =O, —$OR^b$, —$NR^cR^c$ —CN, —$S(O)_2R^b$, —$C(O)NR^cR^c$, —NH—alkyl, —$CH_2OH$, where $R^a$ is selected from the group consisting of alkyl, cycloalkyl, aryl, substituted aryl, imidazolyl, substituted imidazolyl, pyrrolyl, piperidinyl, and triazolyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S.

* * * * *

UNITED STATES PATENT AND TRADEMARK OFFICE
CERTIFICATE OF CORRECTION

PATENT NO.        : 9,000,151 B2
APPLICATION NO.   : 14/184245
DATED             : April 7, 2015
INVENTOR(S)       : Sara Adamski-Werner It is certified that error appears in the above-identified patent and that said Letters Patent is hereby corrected as shown below:

Title page

In column 1 (page 2, item 56) at line 58, Under Other Publications, change "Nucleside" to --Nucleoside--.

In column 1 (page 2, item 56) at line 67, Under Other Publications, change "o." to --Co.--.

In column 2 (page 2, item 56) at line 37, Under Other Publications, change "0xoimidazo" to --Oxoimidazo--.

In column 2 (page 2, item 56) at line 49, Under Other Publications, change "Inhibito,"" to --Inhibitor,"--.

In column 1 (page 3, item 56) at line 52, Under Other Publications, change "(Acesulfam-K),"" to --(Acesulfame-K),"--.

In column 2 (page 4, item 56) at line 11, Under Other Publications, change "Pyrididine" to --Pyridine--.

In column 2 (page 4, item 56) at line 20, Under Other Publications, change "Thrope" to --Thorpe--.

Specification

In column 3 at line 58, Change ""cycloakanyl"" to --"cycloalkanyl"--.

In column 4 at line 38, Change "hexylene," to --hexalene,--.

In column 5 at line 34, Change "alkynyenel" to --alkynylene--.

In column 7 at line 33, Change "heteroarylakenyl" to --heteroarylalkenyl--.

In column 8 at line 33, Change "substitued" to --substituted--.

In column 8 at line 42, Change "—P(O)(OR$^b$)(O)," to -- —P(O)(OR$^b$)(O$^-$),--.

In column 9 at line 5, Change "—P(O)(OR$^b$)(O)," to -- —P(O)(OR$^b$)(O$^-$),--.

In column 9 at line 10, Change "—NR$^b$C(O)NR$^c$R$^{c}$" to -- —NR$^b$C(O)NR$^c$R$^c$,--.

Signed and Sealed this
Twenty-second Day of March, 2016

Michelle K. Lee
*Director of the United States Patent and Trademark Office*

CERTIFICATE OF CORRECTION (continued)
U.S. Pat. No. 9,000,151 B2

Specification

In column 9 at line 22, Change "—$NR^bC(NR^b)NR^cR^c$" to -- —$NR^bC(NR^b)NR^cR^c$,--.

In column 11 at line 52, Change "enhancerscan" to --enhancers can--.

In column 12 at line 14 (approx.), Change "amout" to --amount--.

In column 12 at line 56, Change "cylclopentyl," to --cyclopentyl,--.

In column 13 at line 27 (approx.), Change "cylclopentyl," to --cyclopentyl,--.

In column 21 at line 63, Change "presnet" to --present--.

In column 22 at line 5 (approx.), Change "high fructose corm syrup" to --high fructose corn syrup--.

In column 23 at line 42, Change "drinks" to --drinks.--.

In column 24 at line 57, Change "note" to --not--.

In column 26 at line 57, Change "ingestable" to --ingestible--.

In column 29 at line 66, Change "Feiser and Feiser's" to --Fieser and Fieser's--.

In column 30 at line 3, Change "hetereoaryl," to --heteroaryl,--.

In column 33 at line 28 (approx.), Change "$(MH^1)$." to --$(MH^+)$.--.

Claims

In column 47 at line 52, In Claim 4, change "cylclopentyl," to --cyclopentyl,--.

In column 48 at line 26, In Claim 10, change "cylclopentyl," to --cyclopentyl,--.

In column 56 at line 18 (approx.), In Claim 13, change "—$NR^cR^c$" to -- —$NR^cR^c$,--.